(12) United States Patent
Bhat et al.

(10) Patent No.: US 11,203,585 B2
(45) Date of Patent: Dec. 21, 2021

(54) CRYSTALLINE FORMS OF LENALIDOMIDE

(71) Applicant: BIOCON LIMITED, Bangalore (IN)

(72) Inventors: Ramakrishna Parameswar Bhat, Dhareshwar (IN); Lankeswararao Matti, Remalavaripalem (IN); Venkata Raghavendracharyulu Palle, Mudigere (IN); VijayBhaskar Reddy Regalla, Chatrai (IN)

(73) Assignee: BIOCON LIMITED, Electronic (IN)

( * ) Notice: Subject to any disclaimer, the term of this patent is extended or adjusted under 35 U.S.C. 154(b) by 0 days.

(21) Appl. No.: 16/832,112

(22) Filed: Mar. 27, 2020

(65) Prior Publication Data

US 2020/0347027 A1 Nov. 5, 2020

Related U.S. Application Data

(63) Continuation of application No. PCT/IB2018/057500, filed on Sep. 27, 2018.

(30) Foreign Application Priority Data

Sep. 27, 2017 (IN) .............................. 201741034364

(51) Int. Cl.
*C07D 401/04* (2006.01)
*C07D 275/06* (2006.01)

(52) U.S. Cl.
CPC ......... *C07D 401/04* (2013.01); *C07D 275/06* (2013.01); *C07B 2200/13* (2013.01)

(58) Field of Classification Search
CPC .................................................. C07D 401/04
See application file for complete search history.

(56) References Cited

U.S. PATENT DOCUMENTS 9,695,146 B2 * 7/2017 Stahly .................... A61K 47/12

FOREIGN PATENT DOCUMENTS

WO 2013012485 A2 1/2013
WO 2014160686 A1 10/2014

OTHER PUBLICATIONS

Dean "Analytical Chem . . . " p. 10.24-10.26 (1995).*
Seddon "Pseudopolymorph . . . " Crystal Growth & design v.4(6) p. 1087 (2004) (2 pages from internet).*
Ivanisevic et al., "Use of X-ray . . . "Pharm. Sci. Encycl. p. 1-42 (2010).*
Ivanisevic et al., "Uses of X-ray, etc.," Pharm. Form. Qual. 2011, pp. 30-33.*
Bhattacharya et al., "Thermoanalytical and Crystallographic Methods" in Brittain H. ed., 2nd ed. Informa Healthcare:NY2009 p. 318-335.*
Sekhon BS, "Pharmaceutical co-cyrstals, etc." Ars Pharm., 50(2): 99-117 (2009).*
Kirk-Othmer Encyclopedia of Chemical Technology, 8, pp. 95-147 (2002).*
Stahly, "Diversity in Single-, etc.", Crystal Growth & Design, 7 (6), 2007, 1007-1026.*
Vippagunta et al., "Crystalline Solids", Advanced Drug Delivery Reviews 48 (2001) 3-26.*
Braga et al., "Making crystals from . . . " J. Royal Soc. Chem. Commun. p. 3635-3645 (2005).*
Davidovich et al., "Detection of polymorphism . . . " Am. Pharm. Rev. v.&(1) p. 10, 12, 14, 16, 100 (2004).*
International Search Report for PCT/IB2018/057500, dated Apr. 4, 2019.
Song, et al. "Improving the Solubility of Lenalidomide via Cocrystals", Cryst. Growth Des., 2014, 14, 30693077.

* cited by examiner

*Primary Examiner* — Patricia L Morris
(74) *Attorney, Agent, or Firm* — Katten Muchin Rosenman LLP

(57) ABSTRACT

The present invention provides for novel co-crystals of lenalidomide. The present invention particularly provides for novel cocrystals of lenalidomide with Resorcinol, Methyl paraben and Saccharin. The present invention also provides for the processes for the production of cocrystals of lenalidomide with Resorcinol, Methyl paraben and Saccharin. The present invention further provides for processes for the preparation of crystalline anhydrous lenalidomide Form IV.

5 Claims, 10 Drawing Sheets

CRYSTALLINE FORMS OF LENALIDOMIDE

RELATED APPLICATION

This application is a continuation application of International Application No. PCT/IB2018/057500 filed Sep. 27, 2018, which claims the benefit of IN Patent Application 201741034364 filed Sep. 27, 2017, each of which is herein incorporated by reference in its entirety for all purposes.

TECHNICAL FIELD

The present invention relates to polymorphic forms of Lenalidomide. In particular, the invention relates to co-crystals of lenalidomide and processes for the preparation thereof. This invention also relates to processes for the preparation of crystalline anhydrous lenalidomide.

Formula I

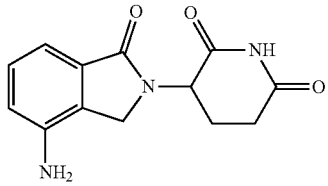

BACKGROUND AND PRIOR ART OF THE DISCLOSURE

REVLIMID® (Lenalidomide), a thalidomide analogue, is an immunomodulatory agent with antiangiogenic and anti-neoplastic properties. The chemical name for Lenalidomide is is 3(4-amino-1-oxo 1,3-dihydro-2H-isoindol-2-yl) piperidine-2,6-dione which is having molecular Formula $C_{13}H_{13}N_3O_3$ and molecular weight 259.3 and its structural Formula is as follows,

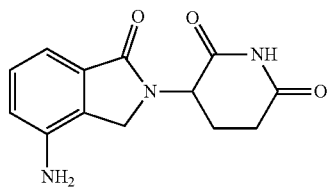 [SMILES: Nc1cccc2c1CN(C1CCC(=O)NC1=O)C2=O]

Lenalidomide inhibits proliferation and induces apoptosis of certain hematopoietic tumor cells including multiple myeloma, mantle cell lymphoma, and del (5q) myelodysplastic syndromes in vitro. Lenalidomide causes a delay in tumor growth in some in vivo nonclinical hematopoietic tumor models including multiple myeloma. Immunomodulatory properties of lenalidomide include activation of T cells and natural killer (NK) cells, increased numbers of NKT cells, and inhibition of pro-inflammatory cytokines (e.g., TNF-α and IL-6) by monocytes.

Lenalidomide which was disclosed in U.S. Pat. No. 5,635,517. Lenalidomide, chemically 3(4-amino-1-oxo 1, 3-dihydro-2H-isoindol-2-yl) piperidine-2, 6-dione.

Lenalidomide is known to exist in various solid-state forms.

U.S. Pat. No. 7,977,357 B2 discloses Form A as an unsolvated, crystalline material that can be obtained from non-aqueous solvent systems; Form B as a hemihydrated, crystalline material that can be obtained from various solvent systems; Form C as a hemisolvated crystalline material that can be obtained from solvents; Form D as a crystalline, solvated polymorph prepared from a mixture of acetonitrile and water; Form E as a dihydrated, crystalline material; Form F as an unsolvated, crystalline material that can be obtained from the dehydration of Form E. Form G as an unsolvated, crystalline material that can be obtained from slurrying forms B and E in a solvent such as, but not limited to, tetrahydrofuran (THF). Form H as a partially hydrated crystalline material that can be obtained by exposing Form E to 0% relative humidity.

PCT publication WO/2010/061209 A1 discloses a crystalline form of anhydrous lenalidomide.

PCT publication WO/2010/129636 A1 discloses a Crystalline Form I of lenalidomide which may be characterized by a PXRD pattern comprising one or more characteristic peaks located at about 8.9, 25.9 and 27.5±0.2 degrees 2-theta.

PCT publication WO/2010/056384 A1 discloses a solvate of lenalidomide with N,N-dimethylformamide (DMF), and a solvate of lenalidomide with dimethylsulfoxide (DMSO). Dimethylformamide solvate of lenalidomide may be characterized by XRPD pattern having characteristic peaks at about 7.9, 8.5, 8.7, 12.1, 14.1, 14.5, 15.1, 15.8, 17.0, 17.9, 18.8, 19.6, 21.6, 22.0, 22.8, 23.3, 24.0, 24.4, 25.4, 26.6, and 26.9, ±0.2 degrees 2-theta. Dimethylsulfoxide solvate of lenalidomide may be characterized by an XRPD pattern having peaks at about 7.7, 8.8, 14.0, 14.6, 15.5, 15.9, 16.4, 17.4, 18.7, 19.5, 20.3, 21.0, 21.9, 22.3, 23.6, 24.6, 25.3, and 27.9, ±0.2 degrees 2-theta.

U.S. Pat. No. 8,420,672 B2 discloses a crystalline form of lenalidomide quarterhydrate (1:0.25). The crystalline form may be characterized by an XRPD pattern having peaks at about 12.1±0.2, 12.6±0.2, 13.4±0.2, 18.9±0.2, 20.0±0.2, 23.9±0.2, 24.7±0.2, 25.8±0.2, and 28.6±0.2 degrees in two theta.

U.S. Pat. No. 9,108,945 B2 discloses a crystalline form of anhydrous lenalidomide having weight loss of up to 0.13% between 25 and 225° C. by thermogravimetric analysis. The crystalline form may be further characterized by an XRPD pattern having peaks at about 10.175±0.2, 11.269±0.2, 15.772±0.2, 16.277±0.2, 17.646±0.2, 20.0990.2, 24.098±0.2, 25.230±0.2, 25.987±0.2, 28.320±0.2, and 32.595±0.2 degrees 2θ.

U.S. Pat. No. 9,808,450 B2 discloses co-crystals of lenalidomide with a coformer; wherein the coformer is benzoic acid, glycolic acid, hippuric acid, magnesium bromide, sodium lauryl sulfate, vanillic acid, or zinc chloride.

U.S. Pat. No. 9,540,341 B2 discloses co-crystals comprising Lenalidomide and a compound selected from Urea, or Gallic acid, or Propyl gallate, or Oxalic acid, or Malonic acid, or Ammonium chloride, or DL-tartaric acid, or L-tartaric acid.

Chinese patent application CN105837556 A discloses co-crystal of lenalidomide with nicotinamide.

SUMMARY OF THE INVENTION

Aspects of the present application provides co-crystals of lenalidomide and safe, simpler & economical processes for the preparation thereof. Each step of the process disclosed herein are contemplated both in the context of the multistep sequences described and individually.

First aspect of the present invention provides crystalline Lenalidomide co-crystal of Formula V.

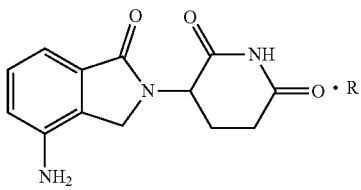

Formula V

Wherein R is a co-former selected from Resorcinol or Methyl paraben or Saccharin.

Second aspect of the present invention provides the crystalline Lenalidomide-Resorcinol co-crystal of Formula Va characterized by ${}^1$H NMR which is in accordance with the FIG. 1.

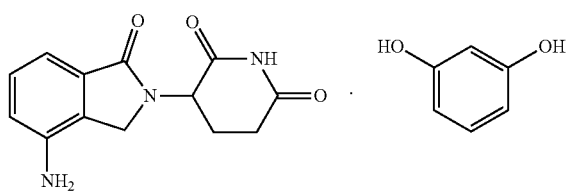

Formula Va

Third aspect of the present invention provides the crystalline Lenalidomide-Resorcinol co-crystal of Formula Va which is further characterized by DSC having endotherm at around 200±3° C. and the DSC pattern in accordance with the FIG. 2.

Fourth aspect of the present invention provides the crystalline Lenalidomide-Resorcinol co-crystal of Formula Va which is further characterised by PXRD having the main 2-theta values 7.20±0.2, 12.90±0.2, 14.50±0.2, 19.60±0.2 and the PXRD pattern in accordance with the FIG. 3.

TABLE 1

| Num. | Gonio | d | Int | I/Imax |
|---|---|---|---|---|
| 1 | 7.0004 | 12.6171 | 274 | 22.8 |
| 2 | 10.8946 | 8.11422 | 53 | 4.4 |
| 3 | 12.7807 | 6.92086 | 1203 | 100.0 |
| 4 | 13.3526 | 6.62568 | 75 | 6.3 |
| 5 | 13.9854 | 6.32728 | 1093 | 90.8 |
| 6 | 14.2399 | 6.21477 | 322 | 26.8 |
| 7 | 14.8249 | 5.97082 | 152 | 12.7 |
| 8 | 15.1968 | 5.82551 | 91 | 7.6 |
| 9 | 15.4538 | 5.72921 | 83 | 6.9 |
| 10 | 16.1904 | 5.47018 | 398 | 33.1 |
| 11 | 17.9586 | 4.93535 | 64 | 5.3 |
| 12 | 18.4611 | 4.80214 | 34 | 2.8 |
| 13 | 19.4178 | 4.56765 | 301 | 25.0 |
| 14 | 20.2083 | 4.39073 | 38 | 3.2 |
| 15 | 21.5045 | 4.12891 | 268 | 22.3 |
| 16 | 21.6828 | 4.09535 | 243 | 30.2 |
| 17 | 22.0361 | 4.03049 | 86 | 7.2 |
| 18 | 23.3210 | 3.81125 | 48 | 4.0 |
| 19 | 24.1929 | 3.67584 | 54 | 4.5 |
| 20 | 24.7960 | 3.58778 | 345 | 28.6 |
| 21 | 25.2979 | 3.51773 | 135 | 11.3 |
| 22 | 25.7618 | 3.45542 | 1200 | 99.7 |
| 23 | 26.1444 | 3.40571 | 108 | 9.0 |
| 24 | 26.6204 | 3.34589 | 282 | 23.4 |
| 25 | 27.8138 | 3.20498 | 59 | 4.9 |
| 26 | 28.2636 | 3.15499 | 177 | 14.7 |
| 27 | 29.0616 | 3.07014 | 62 | 5.2 |
| 28 | 30.2935 | 2.94805 | 51 | 4.2 |
| 29 | 31.0125 | 2.88131 | 54 | 4.5 |

TABLE 1-continued

| Num. | Gonio | d | Int | I/Imax |
|---|---|---|---|---|
| 30 | 32.5655 | 2.74737 | 66 | 5.5 |
| 31 | 33.2286 | 2.69404 | 75 | 6.2 |
| 32 | 34.0164 | 2.63343 | 64 | 5.3 |
| 33 | 35.1282 | 2.55258 | 59 | 4.9 |
| 34 | 36.2109 | 2.47871 | 38 | 3.1 |
| 35 | 37.1185 | 2.42016 | 26 | 2.2 |
| 36 | 38.0975 | 2.36019 | 88 | 7.3 |
| 37 | 38.5910 | 2.33113 | 54 | 4.5 |
| 38 | 40.5217 | 2.2244 | 34 | 2.8 |
| 39 | 41.8707 | 2.1558 | 36 | 3.0 |
| 40 | 42.8864 | 2.10707 | 35 | 2.9 |
| 41 | 44.0647 | 2.05342 | 48 | 4.0 |
| 42 | 45.3335 | 1.99886 | 42 | 3.5 |
| 43 | 46.1030 | 1.96727 | 32 | 2.7 |
| 44 | 46.5645 | 1.94884 | 37 | 3.1 |
| 45 | 46.9624 | 1.93325 | 31 | 2.6 |

Fifth aspect of the present invention provides the process for the preparation of crystalline Lenalidomide-Resorcinol co-crystal of Formula Va.

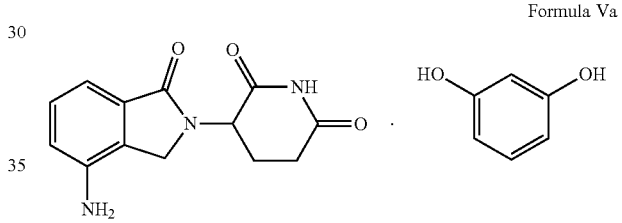

Formula Va comprising the following steps,
Reduction of the Nitro intermediate of Formula II

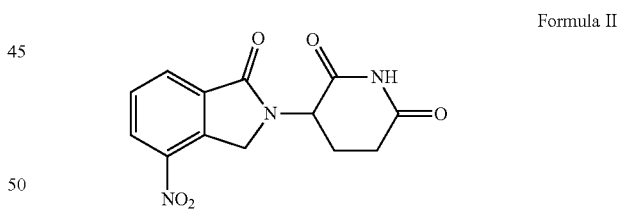

Formula II in a suitable solvent at a suitable temperature in presence of a suitable acid to obtain a salt of Formula I

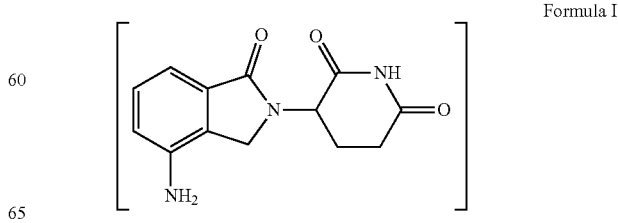

Formula I in situ treatment with Resorcinol in a suitable solvent/s at a suitable temperature,

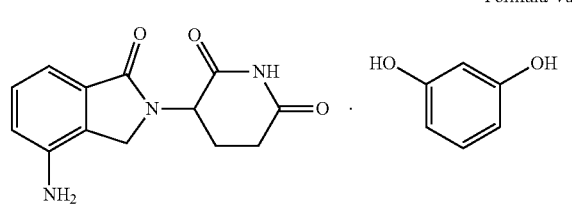

Formula Va to obtain crystalline Lenalidomide-Resorcinol co-crystal of Formula Va.

Further, the present invention relates to the process for the preparation for crystalline Lenalidomide-Resorcinol co-crystal of Formula Va comprising following steps, (i) Reducing the compound of formula II using a suitable reagent in presence and a suitable acid in a suitable solvent at a suitable temperature to obtain a salt of Formula I (ii) Adjusting the pH of the solution containing formula I using a suitable base to a suitable range (iii) Adding suitable equivalents of coformer-resorcinol (iv) Stirring the reaction mixture at a suitable temperature (v) Filtering the reaction mixture at a suitable temperature (vi) Washing the solid with a suitable solvent/solution (vii) Drying the wet solid at a suitable temperature/vacuum to obtain a novel crystalline Lenalidomide-Resorcinol co-crystal of Formula Va.

Further, the invention encompasses the process for the preparation of a novel Lenalidomide-Resorcinol cocrystal of Formula Va consisting of the following wherein, In step (i) suitable reagent contains but not limited to Pd/C. Suitable solvent is selected from aqueous or organic solvents.

Further, the suitable solvent system is selected from water or a mixture of water and an organic solvent wherein the organic solvent is selected from alcohol preferably but not limited to $C_1$-$C_3$ alcohol.

Further, in step (i), suitable acid is selected from $MeSO_3H$, p-$TolSO_3H$, HCl preferably but not limited to $MeSO_3H$.

Further, in step (i), suitable temperature is selected in the range between 25 and 50° C. preferably between 25 and 30° C.

Further, in step (ii), suitable pH range is selected between 7 and 14 preferably between 7 and 9.

Further, in step (iii), suitable equivalents are selected in the range between 0.5 and 10 preferably between 1.5 and 5.0.

Further, in steps (iv) and (v), suitable temperature is selected in the range between 25 and 90° C., preferably between 25 and 70° C.

Further, in steps (vi), suitable solvent/solution is selected from water or a solution of resorcinol in water.

Further, in steps (vii), suitable temperature is selected in the range between 25 and 90° C., preferably between 45 and 60° C. Suitable vacuum is selected in the range between 500 and 720 mm Hg, preferably between 600 and 720 mm Hg.

Sixth aspect of the present invention provides the crystalline Lenalidomide-Methyl Paraben co-crystal of Formula Vb characterized by $^1$H NMR which is in accordance with the FIG. 4.

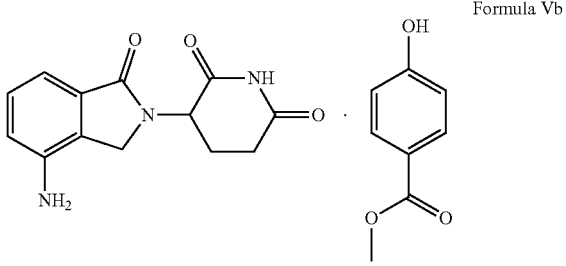

Formula Vb

Seventh aspect of the present invention provides the crystalline Lenalidomide-Methyl Paraben co-crystal of Formula Vb which is further characterized by DSC having endotherm at around 120±5° C. and the DSC pattern in accordance with the FIG. 5.

Eighth aspect of the present invention provides the crystalline Lenalidomide-Methyl Paraben co-crystal of Formula Vb which is further characterised by PXRD having the main 2-theta values 17.12±0.2, 18.69±0.2, 19.15±0.2, 21.47±0.2, 22.54±0.2, 25.27±0.2, 26.37±0.2, 27.69±0.2 and the PXRD pattern in accordance with the FIG. 6.

TABLE 2

| Num. | Gonio | d | Int | I/Imax |
|---|---|---|---|---|
| 1 | | 9.599 | 55 | 5.4 |
| 2 | | 9.17266 | 45 | 4.4 |
| 3 | | 8.79659 | 62 | 6.2 |
| 4 | | 8.31451 | 72 | 7.1 |
| 5 | | 7.47706 | 104 | 10.3 |
| 6 | | 7.11399 | 68 | 6.8 |
| 7 | | 6.98088 | 59 | 5.9 |
| 8 | | 6.27383 | 165 | 16.3 |
| 9 | | 5.90465 | 97 | 9.6 |
| 10 | | 5.78191 | 74 | 7.3 |
| 11 | | 5.68619 | 84 | 8.3 |
| 12 | | 5.49073 | 144 | 14.2 |
| 13 | | 5.25836 | 161 | 15.9 |
| 14 | | 5.17434 | 271 | 26.8 |
| 15 | | 5.0679 | 89 | 8.8 |
| 16 | | 4.92694 | 92 | 9.1 |
| 17 | | 4.74396 | 943 | 93.1 |
| 18 | | 4.63021 | 294 | 29.1 |
| 19 | | 4.40937 | 129 | 12.7 |
| 20 | | 4.1353 | 490 | 48.4 |
| 21 | | 3.94123 | 293 | 28.9 |
| 22 | | 3.79376 | 87 | 8.6 |
| 23 | | 3.7554 | 93 | 9.1 |
| 24 | | 3.72161 | 87 | 8.6 |
| 25 | | 3.52097 | 1013 | 100.0 |
| 26 | | 3.39969 | 213 | 21.0 |
| 27 | | 3.37725 | 279 | 27.6 |
| 28 | | 3.21925 | 238 | 23.5 |
| 29 | | 3.15226 | 91 | 9.0 |
| 30 | | 3.12335 | 69 | 6.9 |
| 31 | | 3.04029 | 66 | 6.5 |
| 32 | | 2.94807 | 71 | 7.0 |
| 33 | | 2.90937 | 65 | 6.5 |
| 34 | | 2.86908 | 42 | 4.1 |
| 35 | | 2.78403 | 59 | 5.8 |
| 36 | | 2.71359 | 59 | 5.8 |
| 37 | | 2.64322 | 54 | 5.3 |
| 38 | | 2.49028 | 52 | 5.2 |
| 39 | | 2.47003 | 97 | 9.5 |
| 40 | | 2.45708 | 120 | 11.8 |
| 41 | | 2.4302 | 56 | 5.5 |
| 42 | | 2.37627 | 68 | 6.7 |
| 43 | | 2.10656 | 47 | 4.6 |
| 44 | | 1.98734 | 36 | 3.5 |

Ninth aspect of the present invention provides the process for the preparation of crystalline Lenalidomide-Methyl Paraben co-crystal of Formula Vb comprising the following steps, Reduction of the Nitro intermediate of Formula II,

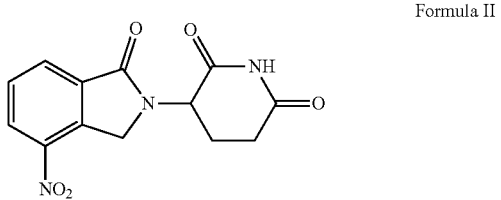 [SMILES: O=C1CCC(N2Cc3c(cccc3[N+](=O)[O-])C2=O)C(=O)N1]

Formula II in a suitable solvent at a suitable temperature to obtain lenalidomide of Formula I

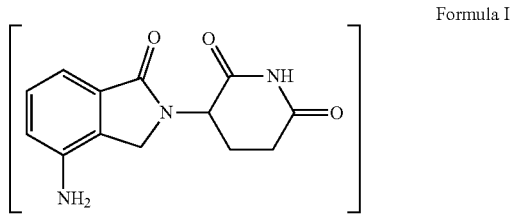

Formula I in situ treatment with Methyl paraben in a suitable solvent/s at a suitable temperature,

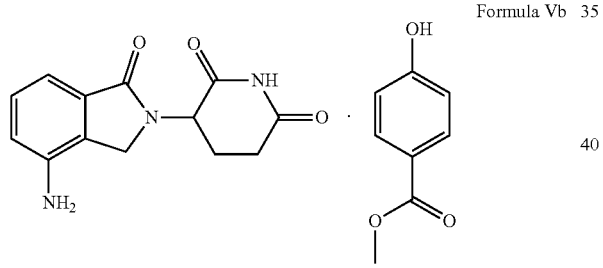

Formula Vb to obtain crystalline Lenalidomide-Methyl paraben co-crystal of Formula Vb.

Further, the present invention relates to the process for the preparation for crystalline Lenalidomide-Methyl paraben co-crystal of Formula Vb comprising following steps, (i) Reducing the compound of formula II using a suitable reagent in a suitable solvent at a suitable temperature to obtain a lenalidomide of Formula I (in situ)
(ii) Adding suitable equivalents of coformer—Methyl Paraben
(iii) Stirring the reaction mixture at a suitable temperature
(iv) Filtering the reaction mixture at a suitable temperature
(v) Optionally washing the solid with a suitable solvent/ solution
(vi) Drying the wet solid at a suitable temperature/vacuum to obtain novel crystalline Lenalidomide-Methyl Paraben co-crystal of Formula Vb.

Further, the invention encompasses the process for the preparation of novel Lenalidomide-Methyl Paraben cocrystal of Formula Vb consisting of the following wherein, In step (i) suitable reagent contains but not limited to Pd/C. Suitable solvent is selected from aqueous or organic solvents.

Further, the suitable solvent is selected from N,N-Dimethylacetamide, N,N-Dimethylformamide etc preferably, N,N-Dimethylacetamide Further, in step (iii), suitable temperature is selected in the range between 25 and 85° C. preferably between 50 and 85° C., more preferably between 75 and 85° C.

Further, in step (ii), suitable equivalents are selected in the range between 0.5 and 10 preferably between 2 and 5.0.

Further, in steps (iii) suitable temperature is selected in the range between 25 and 90° C., preferably between 50 and 90° C.

Further, in step (iv) suitable temperature is selected in the range between 25 and 50° C., preferably between 25 and 35° C.

Further, in steps (v), suitable solvent/solution is selected from water or a solution of Methyl paraben in water.

Further, in steps (vi), suitable temperature is selected in the range between 25 and 90° C., preferably between 45 and 80° C. Suitable vacuum is selected in the range between 500 and 720 mm Hg, preferably between 600 and 720 mm Hg.

Tenth aspect of the present invention provides the crystalline Lenalidomide-Saccharin co-crystal of Formula Vc is characterized by $^1$H NMR which is in accordance with the FIG. 7.

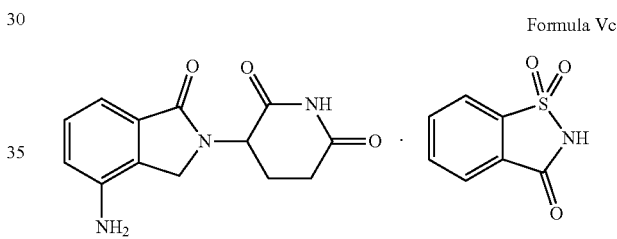

Formula Vc

Eleventh aspect of the present invention provides the crystalline Lenalidomide-Saccharin co-crystal of Formula Vc which is further characterized by DSC having endotherm at around 185±3° C. and the DSC pattern in accordance with the FIG. 8.

Twelfth aspect of the present invention provides the crystalline Lenalidomide-Saccharin co-crystal of Formula Vc which is further characterized by PXRD having the main 2-theta values 15.00±0.2, 16.05±0.2, 19.14±0.2, 20.14±0.2, 22.53±0.2, 25.18±0.2, 25.79±0.2 and the PXRD pattern in accordance with the FIG. 9.

TABLE 3

| Num. | Gonio | d | Int | I/max |
|---|---|---|---|---|
| 1 | 9.5994 | 9.2061 | 171 | 13.0 |
| 2 | 10.6286 | 8.31685 | 140 | 10.6 |
| 3 | 11.8038 | 7.49131 | 208 | 15.8 |
| 4 | 12.6279 | 7.00422 | 96 | 7.3 |
| 5 | 13.7550 | 6.43273 | 49 | 3.7 |
| 6 | 14.9972 | 5.90258 | 349 | 26.5 |
| 7 | 15.5112 | 5.70815 | 102 | 7.7 |
| 8 | 16.0524 | 5.51688 | 686 | 52.1 |
| 9 | 16.8357 | 5.26193 | 158 | 12.0 |
| 10 | 18.1773 | 4.87647 | 131 | 10.0 |
| 11 | 19.1405 | 4.6332 | 868 | 66.0 |
| 12 | 20.1460 | 4.40416 | 342 | 26.0 |
| 13 | 20.4278 | 4.34404 | 53 | 4.0 |
| 14 | 21.5780 | 4.11502 | 99 | 7.5 |

TABLE 3-continued

| Num. | Gonio | d | Int | I/max |
|------|-------|---|-----|-------|
| 15 | 22.5326 | 3.94279 | 552 | 41.9 |
| 16 | 22.8343 | 3.89138 | 255 | 19.4 |
| 17 | 23.6415 | 3.76031 | 158 | 12.0 |
| 18 | 23.8930 | 3.72129 | 286 | 21.7 |
| 19 | 25.1771 | 3.53433 | 1316 | 100.0 |
| 20 | 25.7864 | 3.45218 | 320 | 24.3 |
| 21 | 26.4994 | 3.36089 | 118 | 9.0 |
| 22 | 27.4787 | 3.2433 | 145 | 11.1 |
| 23 | 28.0484 | 3.1787 | 110 | 8.3 |
| 24 | 28.3076 | 3.15018 | 141 | 10.7 |
| 25 | 28.8917 | 3.08781 | 41 | 3.1 |
| 26 | 29.4711 | 3.02841 | 84 | 6.4 |
| 27 | 29.7091 | 3.00469 | 39 | 2.9 |
| 28 | 30.5996 | 2.91924 | 108 | 8.2 |
| 29 | 30.9480 | 2.88717 | 80 | 6.1 |
| 30 | 32.1237 | 2.78414 | 109 | 8.2 |
| 31 | 33.8474 | 2.64619 | 115 | 8.7 |
| 32 | 34.3332 | 2.60985 | 40 | 3.0 |
| 33 | 35.0748 | 2.55635 | 95 | 7.2 |
| 34 | 36.0271 | 2.49093 | 60 | 4.6 |
| 35 | 36.6844 | 2.44779 | 36 | 2.7 |
| 36 | 37.2458 | 2.41218 | 33 | 2.5 |
| 37 | 37.9759 | 2.36746 | 33 | 2.5 |
| 38 | 38.4084 | 2.3418 | 41 | 3.1 |
| 39 | 39.0248 | 2.30621 | 44 | 3.3 |
| 40 | 39.8935 | 2.25797 | 33 | 2.5 |
| 41 | 40.2564 | 2.23845 | 37 | 2.8 |
| 42 | 41.5502 | 2.17169 | 48 | 3.6 |

Thirteenth aspect of the present invention provides the process for the preparation of crystalline Lenalidomide-Saccharin co-crystal of Formula Vc comprising the following steps, Reduction of the Nitro intermediate of Formula II

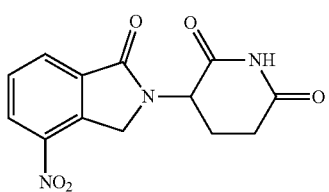

Formula II in a suitable solvent at a suitable temperature to obtain lenalidomide of Formula I

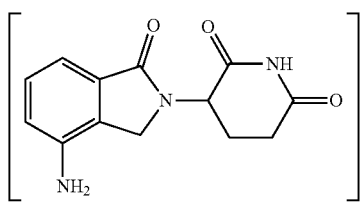

Formula-I in situ treating with Saccharin in a suitable solvent/s at a suitable temperature,

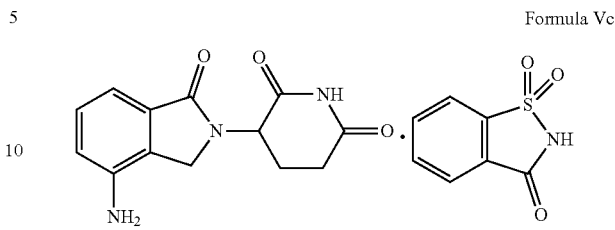

Formula Vc to obtain crystalline Lenalidomide-Saccharin co-crystal of Formula Vc.

Further, the present invention relates to the process for the preparation for crystalline Lenalidomide-Saccharin co-crystal of Formula Vc comprising following steps, (i) Reducing the compound of formula II using a suitable reagent in a suitable solvent at a suitable temperature to obtain a lenalidomide of Formula I (in situ)

(ii) Adding suitable equivalents of coformer—Saccharin (iii) Stirring the reaction mixture at a suitable temperature (iv) Adding a suitable anti-solvent (v) Filtering the reaction mixture (v) Washing the solid with a suitable solvent/solution (vi) Drying the wet solid at a suitable temperature/vacuum to obtain novel crystalline Lenalidomide-Saccharin co-crystal of Formula Vc.

Further, the invention encompasses the process for the preparation of novel Lenalidomide-Saccharin co-crystal of Formula Vc consisting of the following wherein, In step (i) suitable reagent contains but not limited to Pd/C. Suitable solvent is selected from aqueous or organic solvents.

Further, the suitable solvent system is selected from an organic solvent wherein the organic solvent is from N,N, Dimethyl acetamide and or $C_1$-$C_3$ alcohol preferably but not limited to N,N, Dimethyl acetamide.

Further, in step (i), suitable temperature is selected in the range between 25 and 70° C. preferably between 50 and 70° C.

Further, in step (ii), suitable equivalents are selected in the range between 0.5 and 10 preferably between 2.5 and 5.0.

Further, in step (iii), suitable temperature is selected in the range between 25 and 90° C., preferably between 25 and 70° C.

Further, in steps (iv), suitable solvent/solution is selected from $C_1$-$C_3$ alcohol preferably Methanol.

Further, in steps (vi), suitable temperature is selected in the range between 25 and 90° C., preferably between 45 and 70° C. Suitable vacuum is selected in the range between 500 and 720 mm Hg, preferably between 600 and 720 mm Hg.

Fourteenth aspect of the present invention provides a process for the preparation of crystalline anhydrous lenalidomide Form IV.

TABLE 4

| Num. | Gonio | d | Int | I/Imax |
|------|-------|---|-----|--------|
| 1 | 10.4076 | 8.49297 | 275 | 27.8 |
| 2 | 11.6028 | 7.62064 | 373 | 37.6 |
| 3 | 12.4283 | 7.11626 | 166 | 16.7 |
| 4 | 13.5234 | 6.54239 | 61 | 6.2 |
| 5 | 14.7506 | 6.00072 | 280 | 28.2 |

TABLE 4-continued

| Num. | Gonio | d | Int | I/Imax |
|---|---|---|---|---|
| 6 | 15.7072 | 5.63734 | 91 | 9.2 |
| 7 | 16.6286 | 5.32699 | 283 | 28.6 |
| 8 | 18.0102 | 4.92133 | 258 | 26.1 |
| 9 | 18.9238 | 4.68577 | 982 | 99.0 |
| 10 | 20.2143 | 4.38944 | 86 | 8.7 |
| 11 | 21.5686 | 4.11677 | 72 | 7.3 |
| 12 | 22.3480 | 3.97494 | 991 | 100.0 |
| 13 | 23.0115 | 3.86181 | 56 | 5.7 |
| 14 | 23.4546 | 3.78984 | 255 | 25.8 |
| 15 | 25.1456 | 3.53868 | 66 | 6.7 |
| 16 | 26.3269 | 3.38252 | 178 | 18.0 |
| 17 | 27.1654 | 3.27998 | 90 | 9.1 |
| 18 | 27.3718 | 3.25572 | 96 | 9.7 |
| 19 | 28.0925 | 3.17382 | 227 | 22.9 |
| 20 | 29.5228 | 3.02322 | 55 | 5.5 |
| 21 | 29.9057 | 2.98938 | 37 | 3.7 |
| 22 | 30.5404 | 2.92477 | 157 | 15.8 |
| 23 | 31.9175 | 2.80165 | 107 | 10.8 |
| 24 | 32.6393 | 2.74132 | 32 | 3.3 |
| 25 | 33.7302 | 2.65511 | 93 | 9.4 |
| 26 | 34.8543 | 2.57201 | 31 | 3.1 |
| 27 | 35.7815 | 2.50746 | 97 | 9.7 |
| 28 | 36.5661 | 2.45544 | 54 | 5.5 |
| 29 | 37.0498 | 2.42449 | 29 | 2.9 |
| 30 | 38.2674 | 2.3501 | 25 | 2.6 |
| 31 | 39.0169 | 2.30666 | 32 | 3.2 |
| 32 | 40.1831 | 2.24237 | 21 | 2.1 |
| 33 | 40.8022 | 2.20976 | 21 | 2.1 |
| 34 | 42.7392 | 2.11399 | 37 | 3.7 |
| 35 | 44.0699 | 2.05319 | 29 | 2.9 |
| 36 | 44.4227 | 2.0377 | 32 | 3.3 |
| 37 | 45.7841 | 1.98023 | 44 | 4.5 |
| 38 | 48.1482 | 1.88837 | 24 | 2.4 |
| 39 | 49.4495 | 1.84168 | 20 | 2.0 |

Fifteenth aspect of the present invention provides a process for the preparation of crystalline anhydrous lenalidomide Form IV using novel crystalline forms of lenalidomide co-crystals wherein coformers are selected from resorcinol, Methyl paraben & Saccharin.

Sixteenth aspect of the present invention provides a process for the preparation of crystalline anhydrous lenalidomide Form IV using lenalidomide resorcinol co-crystal of Formula Va, comprising the following steps, i. Heating a slurry of lenalidomide resorcinol co-crystal of Formula Va in a suitable first solvent to a suitable temperature

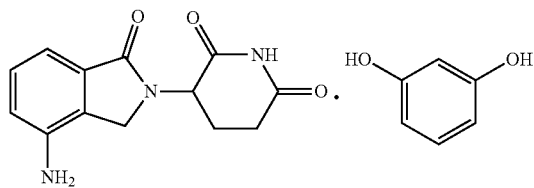

Formula Va to obtain a clear solution.
ii. Cooling the reaction mass to a suitable temperature.
iii. Mixing the reaction mass with a suitable second solvent.
iv. Stirred at room temperature for a suitable period of time.
v. Isolating the crystalline anhydrous lenalidomide Form IV.

Further, the invention encompasses the process for the preparation of crystalline anhydrous lenalidomide Form IV consisting of the following wherein, In step (i) suitable first solvent is selected from N,N-Dimethyl acetamide, N,N-Dimethyl formamide, N,N-Dimethyl sulfoxide or a mixture thereof.

Further, in step (i), suitable temperature is selected in the range between 40 and 70° C. preferably between 50 and 60° C.

Further, in step (iii), suitable second solvent is selected from methanol, ethanol, propanol or a mixture thereof.

Further, in step (iv), suitable temperature is selected from 1 to 4 h, preferably between 1.5 to 2 h.

Seventeenth aspect of the present invention provides a process for the preparation of crystalline anhydrous lenalidomide Form IV using lenalidomide Methyl Paraben co-crystal of Formula Vb, comprising the following steps, i. Heating a slurry of lenalidomide Methyl Paraben co-crystal of Formula Vb in a suitable first solvent to a suitable temperature

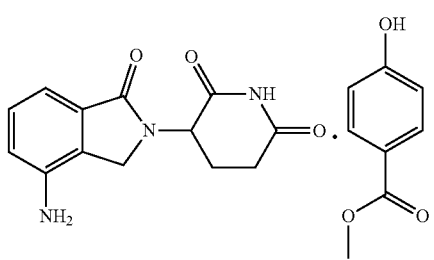

Formula Vb to obtain a clear solution.
ii. Cooling the reaction mass to room temperature.
iii. Mixing the reaction mass with a suitable second solvent.
iv. Stirred at room temperature for a suitable period of time.
v. Isolating the crystalline anhydrous lenalidomide Form IV.

Further, the invention encompasses the process for the preparation of crystalline anhydrous lenalidomide Form IV consisting of the following wherein, In step (i) suitable first solvent is selected from N,N-Dimethyl acetamide, N,N-Dimethyl formamide, N,N-Dimethyl sulfoxide or a mixture thereof.

Further, in step (i), suitable temperature is selected in the range between 40 and 70° C. preferably between 50 and 60° C.

Further, in step (iii), suitable second solvent is selected from methanol, ethanol, propanol or a mixture thereof.

Further, in step (iv), suitable temperature is selected from 1 to 4 h, preferably between 1.5 to 2 h.

Eighteenth aspect of the present invention provides a process for the preparation of crystalline anhydrous lenalidomide Form IV using lenalidomide Saccharin co-crystal of Formula Vc, comprising the following steps, i. Heating a slurry of lenalidomide Saccharin co-crystal of Formula Vc in a suitable first solvent to a suitable temperature Formula Vc

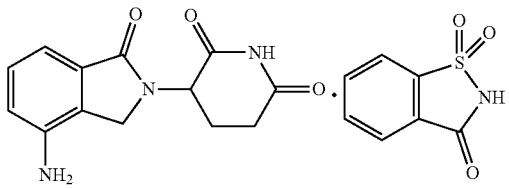

to obtain a clear solution.

ii. Cooling the reaction mass to room temperature.
iii. Mixing the reaction mass with a suitable second solvent.
iv. Stirred at room temperature for a suitable period of time.
v. Isolating the crystalline anhydrous lenalidomide Form IV.

Further, the invention encompasses the process for the preparation of crystalline anhydrous lenalidomide Form IV consisting of the following wherein, In step (i) suitable first solvent is selected from N,N-Dimethyl acetamide, N,N-Dimethyl formamide, N,N-Dimethyl sulfoxide or a mixture thereof.

Further, in step (i), suitable temperature is selected in the range between 40 and 70° C. preferably between 50 and 60° C.

Further, in step (iii), suitable second solvent is selected from methanol, ethanol, propanol or a mixture thereof.

Further, in step (iv), suitable temperature is selected from 1 to 4 h, preferably between 1.5 to 2 h.

Nineteenth aspect of the present invention provides a process for the preparation of crystalline anhydrous lenalidomide Form IV comprising the following steps, Reduction of the Nitro intermediate of Formula II

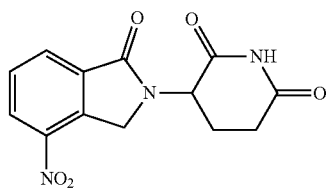

Formula-II in a suitable first solvent at a suitable temperature to obtain lenalidomide of Formula I

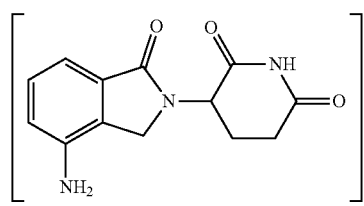

Formula-I in situ treating with a coformer in at a suitable temperature,

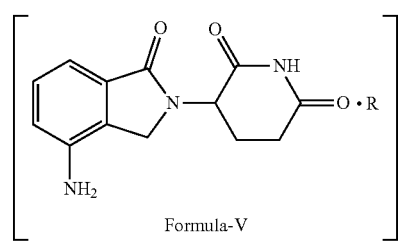

Formula-V to obtain Lenalidomide-co-crystal of Formula V (in-situ).
[Wherein R is a coformer selected from resorcinol, methyl paraben & saccharin.]

Treating the Lenalidomide-co-crystal of Formula V (in-situ) with a suitable second solvent at a suitable temperature, stirring for a suitable period of time to isolate crystalline anhydrous lenalidomide Form IV.

Further, the present invention relates to the process for the preparation for crystalline anhydrous lenalidomide Form IV comprising following steps, (i) Reducing the compound of formula II using a suitable reagent in a suitable solvent at a suitable temperature to obtain a lenalidomide of Formula I (in situ)
(ii) Adding suitable equivalents of coformer [coformer selected from Resorcinol, Methyl paraben & Saccharin]
(iii) Stirring the reaction mixture at a suitable temperature to obtain lenalidomide cocrystal (in situ)
(iv) Treating the above lenalidomide cocrystal (in situ) with a second solvent
(v) Isolating the as obtained solid, washing
(vi) Drying the wet solid at a suitable temperature/vacuum to obtain crystalline anhydrous lenalidomide Form IV.

Further, the invention encompasses the process for the preparation of crystalline anhydrous lenalidomide Form IV consisting of the following wherein, In step (i) suitable reagent contains but not limited to Pd/C. Suitable solvent is selected from aqueous or organic solvents.

Further, the suitable solvent system is selected from water or an organic solvent wherein the organic solvent is selected from N,N-Dimethyl acetamide, N,N-Dimethyl formamide, N,N-Dimethyl sulfoxide.

Further, in step (i), suitable temperature is selected in the range between 50 and 80° C. preferably between 60 and 70° C.

Further, in steps (iv), suitable second solvent is selected from alcoholic solvents, preferably selected from C1-C4 alcohols.

Accordingly, the different crystalline Lenalidomide forms of the present invention are prepared and characterised by orthogonal analytical tools.

Characterization Techniques:

FT-IR, DSC, 1H NMR and PXRD techniques were used for characterising the co-crystal. The infrared spectroscopy, presents a great quantity of information about the chemical bonds and interaction. It is a fast analysis method, non-destructive.

The Powder X-ray diffraction is one of the most used techniques to determine different crystalline structures. This technique can distinguish the presence of a new crystallographic motif, which can be a polymorph or a co-crystal. It is a non-destructive method and presents diffractions patterns unique for each structure.

The differential scanning calorimetry is a characterization method based on the heat of reaction involved in different thermal events. For the pharmaceutical industry, the DSC is mostly used to obtain melting points of the API and thus, determine its purity. For the co-crystal analysis, there is a clear difference between the melting point of the co-former and the co-crystal itself.

Instrumental Parameters:

The H-NMR spectrum recorded in Bruker 400 MHz spectrometer using DMSO-d6 as solvent and chemical shifts are reported in ppm downfield from TMS.

DSC was performed on a Discovery DSC (TA instruments). About 3-5 mg of sample placed in crimped aluminium sample pan to be positioned on auto sampler. The temperature range was from 30-350° C. @ 10° C./min. Samples were purged by a stream of nitrogen flowing at 50 mL/min.

Equilibrate: 30° C.
Ramp: 10° C./min
Range: 30° C.-350° C.

The FT-IR spectrum (Fourier transform R spectroscopy) was recorded using the Fisher Scientific (NICOLET-iS50-FTIR), equipped with a KBr splitter and a DTGS KBr detector. The spectrum was recorded in the range of 4000 cm−1 to 400 cm−1

The powder X-ray powder diffractogram (XRPD) was obtained by using the instrument XRD BRUKER D8 ADVANCE, equipped with LYNXEYE detector with 40 mA current intensity and 40 kV voltage.

The sample was arranged on a Si-Zero background Sample holder and analysed using the following parameters:

Scanning range (°): 3.000 to 60.000
Step size (°): 0.03
Scan type: Locked coupled
Scanning mode: continuous
Count time per step (s): 0.5
Delay time (s): 0
Divergent slit: 0.300
Antiscatter slit: 0.300

Advantages of Present Invention:

An API can exist in a variety of solid state forms, which include: polymorphs; solvates; hydrates; salts; co-crystals and amorphous forms. Each form exhibits unique physiochemical properties that can profoundly influence the bioavailability, stability, manufacturability and other performance characteristics of the Formulated API.

Crystalline forms when compared to the amorphous form often show desired unique physical and/or biological characteristics which usually contributes in the manufacture or Formulation of the active compound, to the purity levels and uniformity required for regulatory approval. Hence, it is desirable to provide the pharmaceutically active ingredient in a substantially pure, crystalline and stable form of API.

Furthermore, the provision of further crystalline forms of a pharmaceutically useful compound offers an opportunity to improve the performance profile of a pharmaceutical product. In particular, not all solid forms of a pharmaceutically useful compound are equally suited for development of a pharmaceutical dosage form. It is therefore desirable to widen the reservoir of materials a Formulation scientist can select from, such that he can design a new dosage form of a drug having improved characteristics.

In simple terms, Co-crystals are an important class of pharmaceutical materials that can enhance solubility and dissolution by forming a crystal of a drug and other benign molecule or co-former with specific stoichiometric compositions.

According to Almarsson and Zaworotko the definition of pharmaceutical co-crystals—co-crystals are those that are formed between an active pharmaceutical ingredient (API) and a co-crystal former (CF), which is a solid under ambient conditions, and is not limited to two components. The components of the crystal interact by hydrogen bond or other noncovalent and non-ionic interactions (Ö. Almarsson, M. J. Zaworotko, "Crystal engineering of the composition of pharmaceutical phases. Do pharmaceutical co-crystals represent a new path to improved medicines?" *Chem. Commun.* 2004, 17, pp. 1889-18%).

Advantages of Novel Crystalline Lenalidomide-Resorcinol Co-Crystal:

Hygroscopicity is lesser or comparable with that of Lenalidomide hemihydrate. Form-C experiences significant weight loss about 6.03% (U.S. Pat. No. 7,465,800 B2). However, novel Lenalidomide-Resorcinol co-crystal does not exhibit significant weight change.

Novel Lenalidomide-Resorcinol co-crystal is thermally stable (neat, at least up to 80° C.).

Water slurry experiment has been performed to understand the relative solubility wrt Lenalidomide hemihydrate. Accordingly, Lenalidomide-Resorcinol co-crystal was slurried with water. PXRD analysis of the sample after 1 day indicated the co-crystal has been transformed to a different form indicating that it is more soluble than the Lenalidomide hemihydrate.

Economical process of preparation.

The procedure involves in-situ synthesis of Lenalidomide co-crystal formation without the isolation of Lenalidomide.

The process for the preparation of novel Lenalidomide-Resorcinol co-crystal is scaleup friendly.

The process for the preparation of novel Lenalidomide-Resorcinol co-crystal does not involve the necessity of inert condition.

Crystalline Anhydrous Lenalidomide Form IV:

This has been discolosed in *Cryst. Growth,* 2017, 17, 612-628. However, the process involves heating of Lenalidomide hemihydrate to a high temperature to obtain Form IV.

The process has following disdavantages.

Not scale up friendly.

Specific temperature (140° C.) is necessary to obtain the desired polymorph i.e. Form IV. Any change in the temperature will result in different polymorphs.

Input is Lenalidomide hemihydrate.

Advantages of Novel Crystalline Lenalidomide-Saccharin Co-Crystal:

Saccharin is pharmaceutically acceptable and listed in FDA Inactive Ingredients.

Saccharin Toxicity-Acute oral toxicity ($LD_{50}$): 17000 mg/kg [Mouse])

Scale up friendly process.

Isolation crystalline Lenalidomide does not involve any Lenalidomide in any forms such as anhydrous, hemihydrate or dihydrate.

BRIEF DESCRIPTION OF THE FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure wherein.

Figure 1:
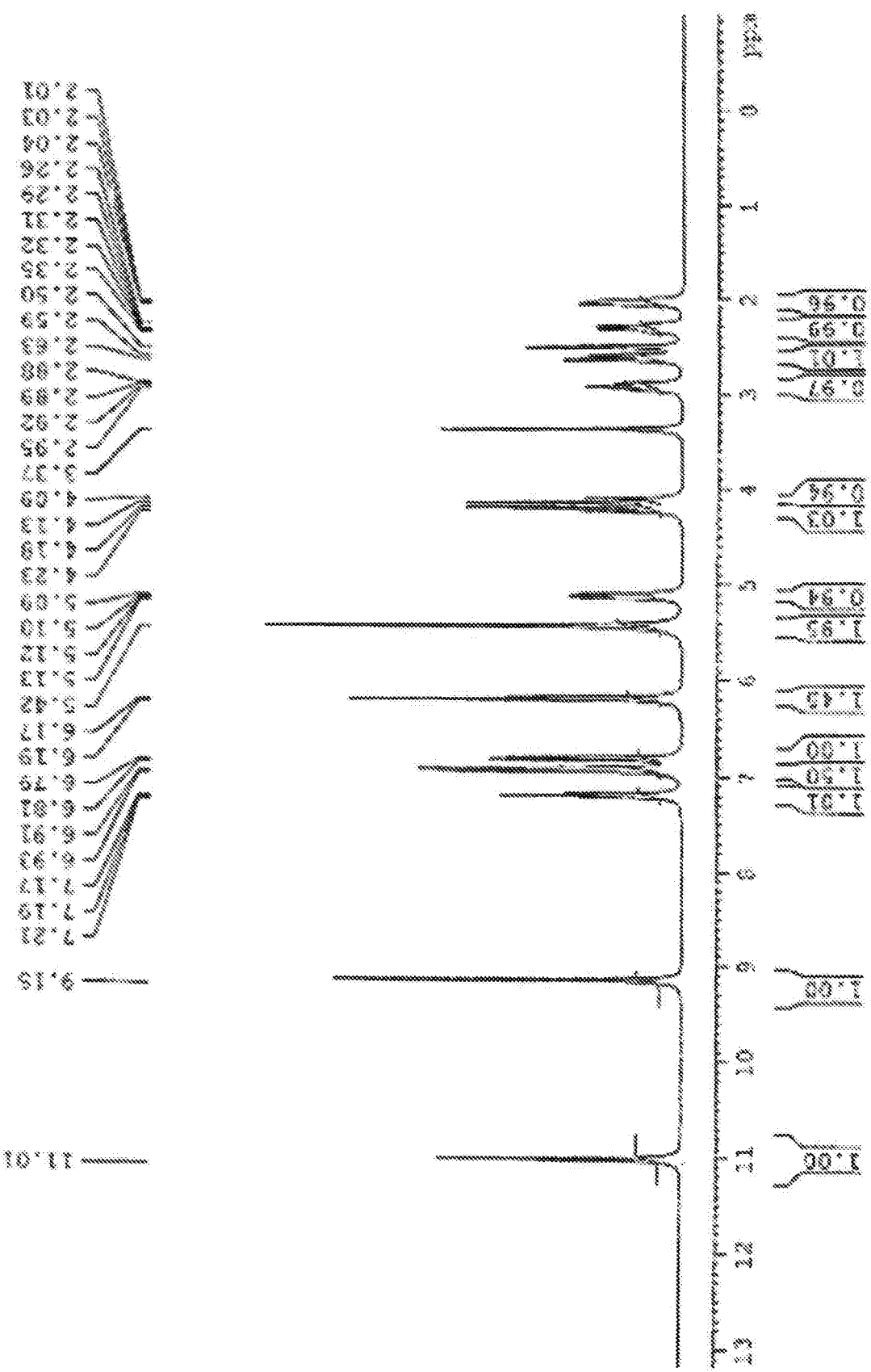
FIG. 1: Illustrates the $^1$H NMR pattern of the crystalline Lenalidomide-Resorcinol co-crystal of Formula Va.
Figure 2:
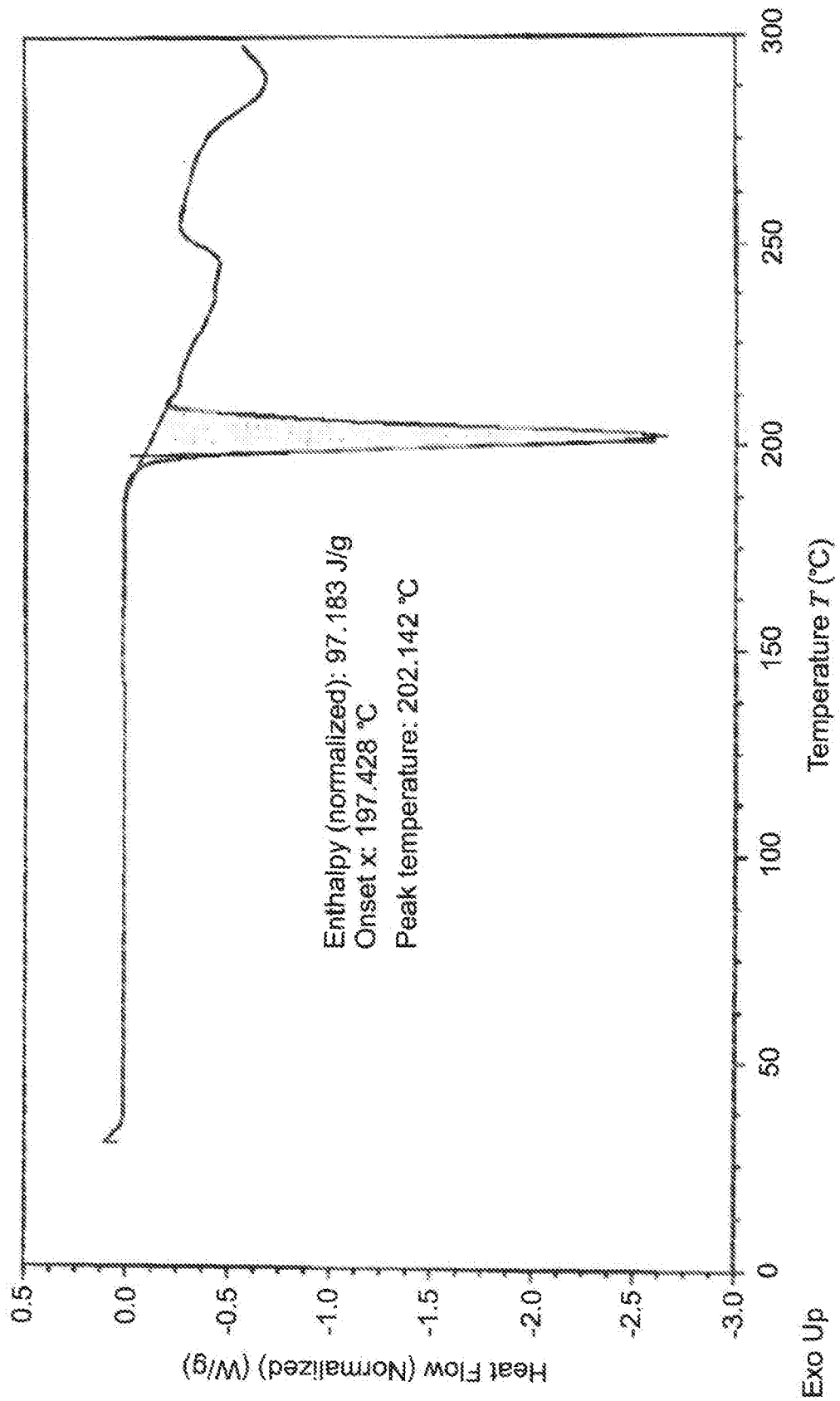
FIG. 2: Illustrates the DSC thermogram of the crystalline Lenalidomide-Resorcinol co-crystal of Formula Va.
Figure 3:
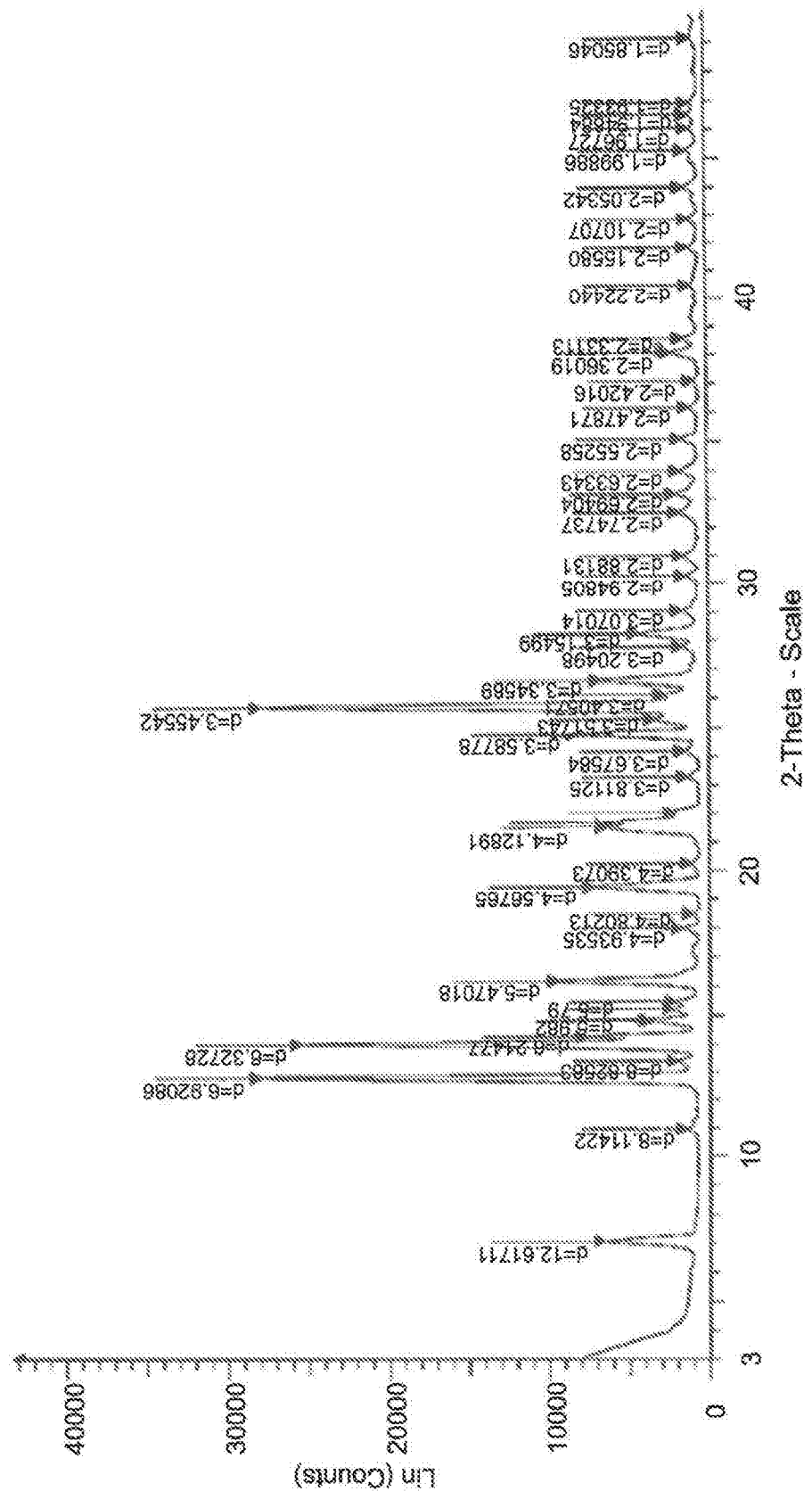
FIG. 3: Illustrates the PXRD of crystalline Lenalidomide-Resorcinol co-crystal of Formula Va.
Figure 4:
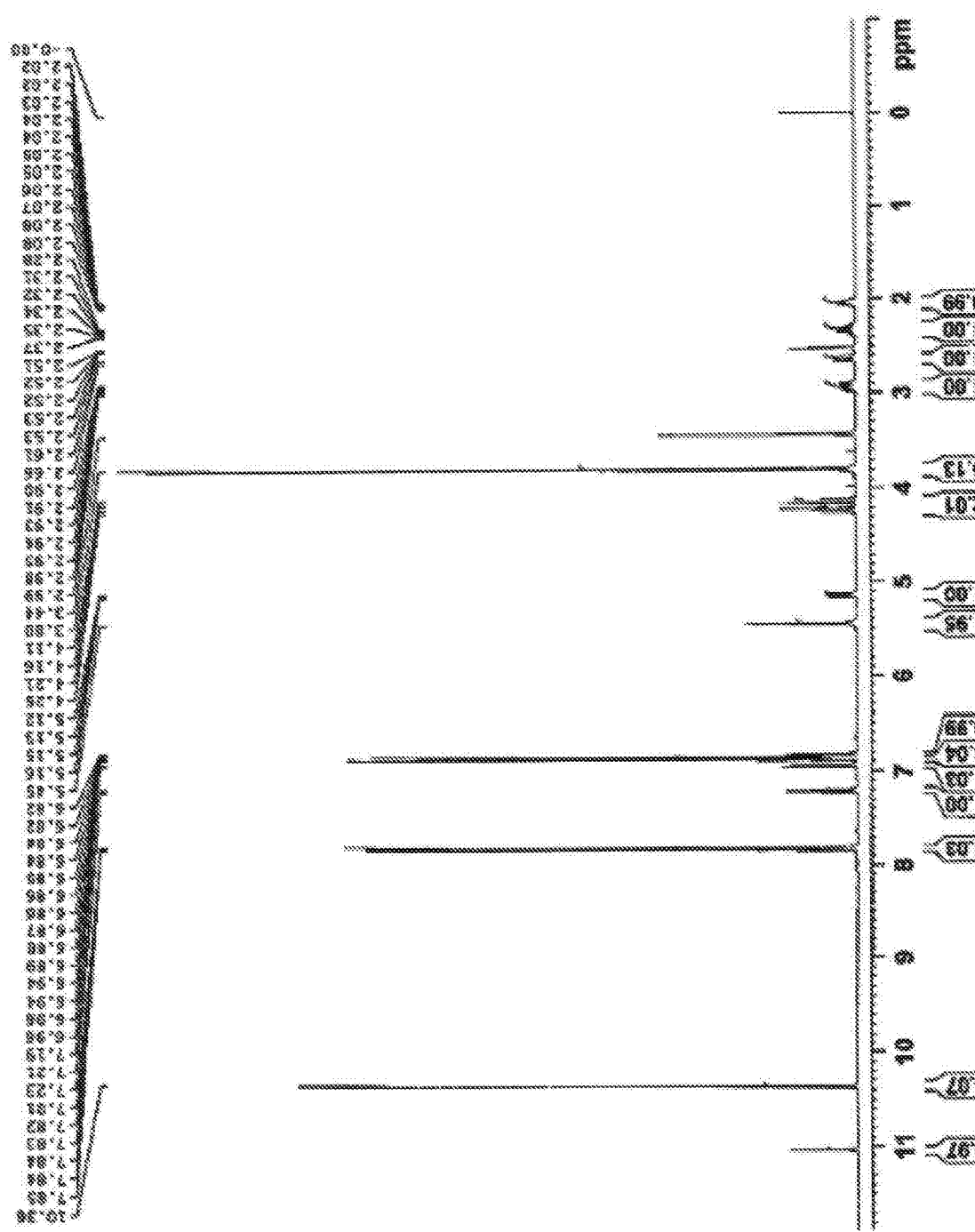
FIG. 4: Illustrates the $^1$H NMR pattern of the crystalline Lenalidomide-Methyl Paraben co-crystal of Formula Vb.
Figure 5:
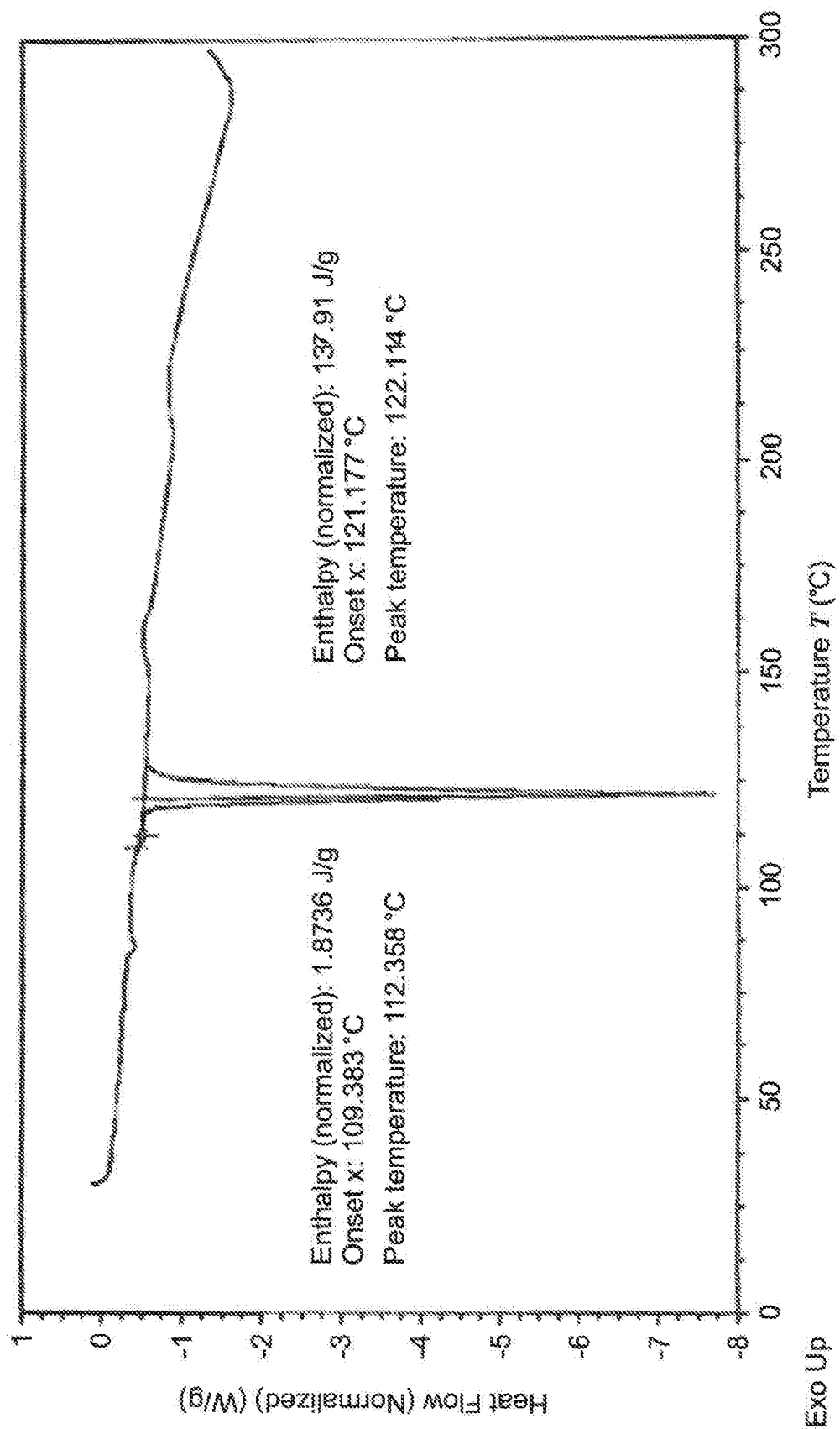
FIG. 5: Illustrates the DSC thermogram of the crystalline Lenalidomide-Methyl Paraben co-crystal of Formula Vb.
Figure 6:
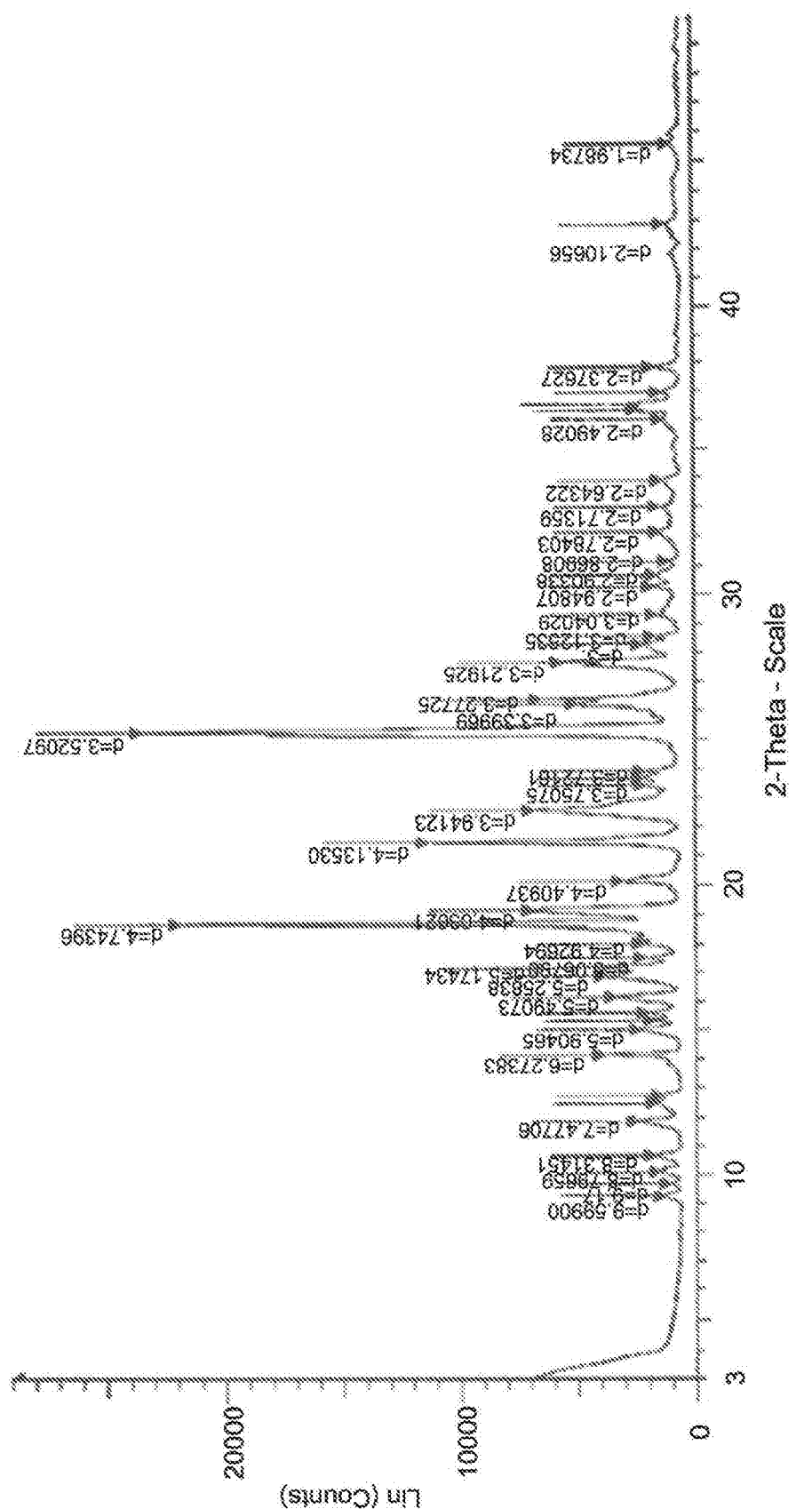
FIG. 6: Illustrates the PXRD of the crystalline Lenalidomide-Methyl Paraben co-crystal of Formula Vb.
Figure 7:
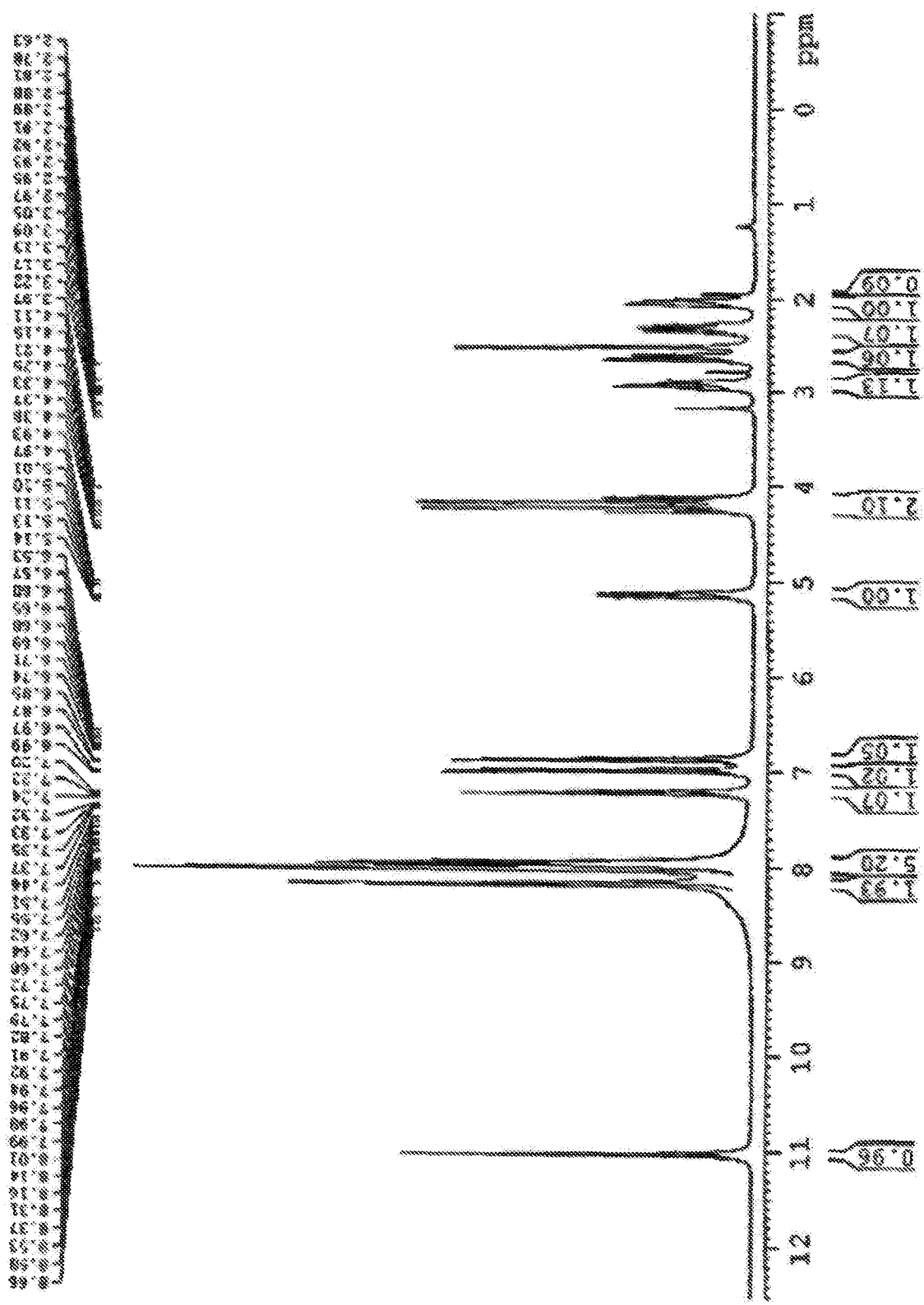
FIG. 7: Illustrates the $^1$H NMR pattern of the crystalline Lenalidomide-Saccharin co-crystal of Formula Vc.

The method of analysis of the compounds represented in the figures as above are as below:

PXRD Analysis

About 300 mg of powder sample was taken onto the sample holder and was tightly packed on the sample holder uniformly by means of glass slide and Powder X-ray diffraction was recorded on Bruker D8 Advance diffractometer (Bruker-AXS, Karlsruhe, Germany) using Cu-Kα X-radiation (k=1.5406 Å) at 40 kV and 30 mA powder. X-ray diffraction patterns were collected over the 2θ range 3-50° at a scan rate of 1°/min.

DSC Analysis

DSC was performed on a Mettler Toledo DSC 822e module. 4-6 mg of sample was placed in crimped but vented aluminium sample pans. The temperature range was from 30-250° C. @ 10° C./min. Samples were purged by a stream of nitrogen flowing at 80 mL/min.

IR Anlaysis

IR was performed on a Fisher Scientific (NICOLET-iS50-FTIR). About 5 mg of sample was spread over the region of diamond ATR sampling station and collected the sample spectrum between 4000 cm−1 to 400 cm−1 to obtain a spectrum of suitable intensity (above 60% transmission at 2000 cm−1).

DETAILED DESCRIPTION OF THE INVENTION

The embodiments of the present invention are further described using specific examples herein after. The examples are provided for better understanding of certain embodiments of the invention and not, in any manner, to limit the scope thereof. Possible modifications and equivalents apparent to those skilled in the art using the teachings of the present description and the general art in the field of the invention shall also form the part of this specification and are intended to be included within the scope of it.

Schemes:

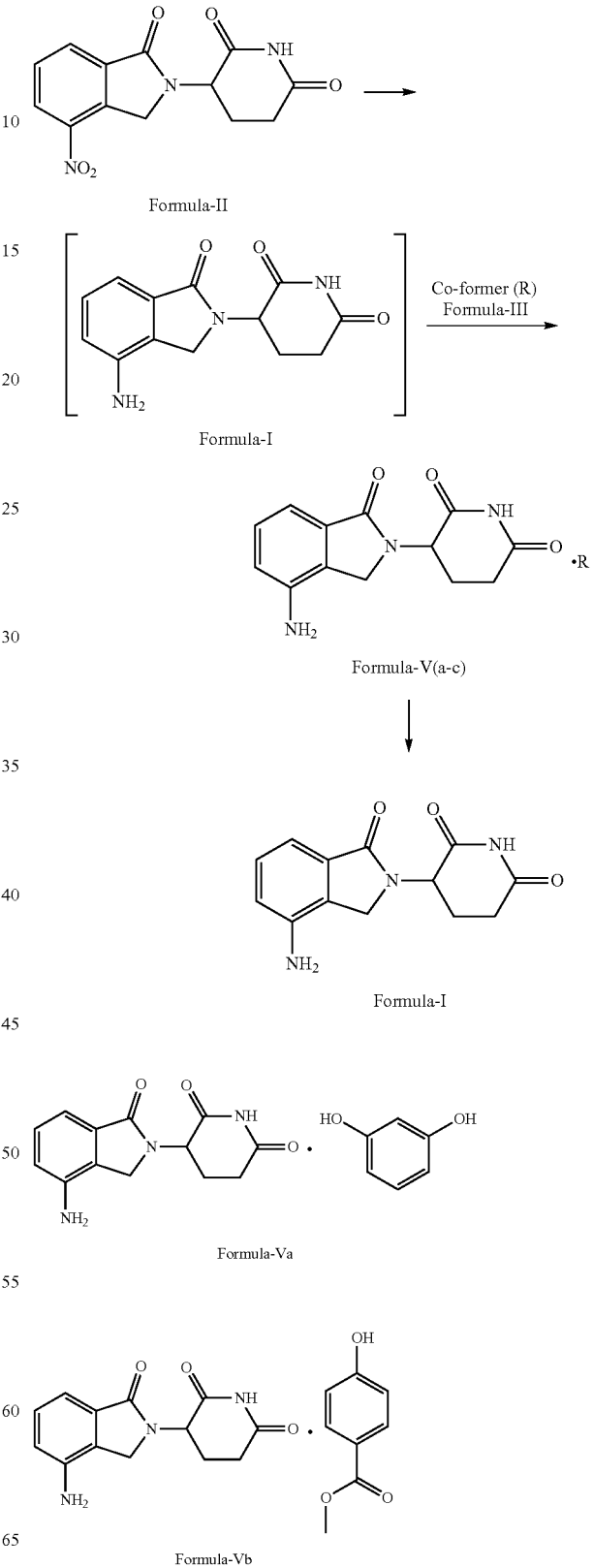

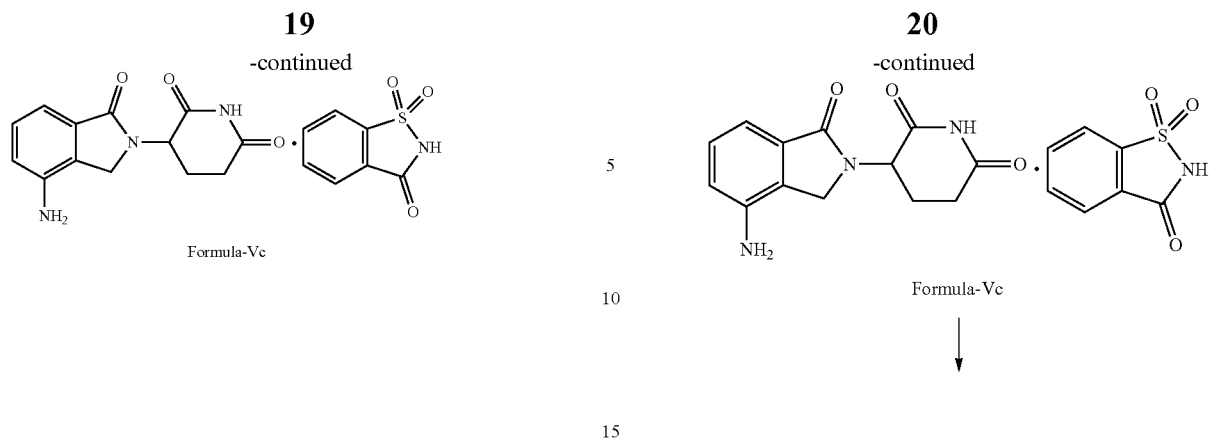

Formula-Vc

Formula-Vc

↓

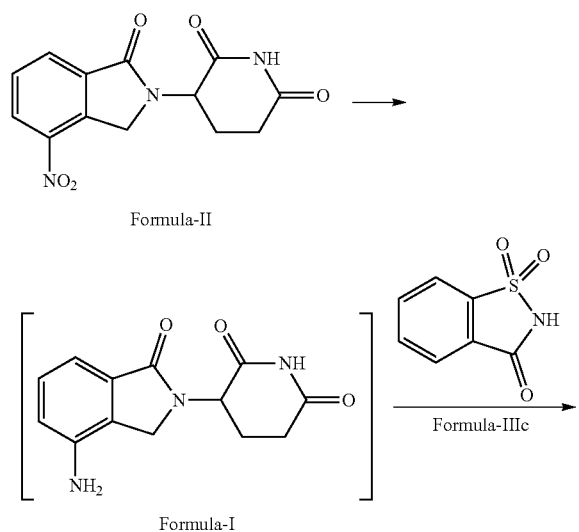

Formula-I

General Example-1

To a hydrogenator were added Formula II, a suitable solvent and a hydrogenation catalyst. The reaction mass was stirred under $H_2$ atmosphere at a suitable temperature for a suitable amount of time. After completion of the reaction the reaction mass was cooled, filtered and the product as obtained in solution is subjected to charcoalisation followed by treatment with a suitable coformer R [wherein R is selected from Resorcinol, Methyl Paraben & Saccharin], stirred at a suitable temperature for a suitable amount of time and isolated crystalline lenalidomide cocrystal of Formula V. The crystalline lenalidomide cocrystal of Formula V was dissolved in a suitable first solvent, heated to a suitable temperature and cooled to a suitable temperature followed by addition of a second solvent. The reaction mass was stirred for a suitable duration and isolated crystalline anhydrous lenalidomide Form IV.

As explained above the crystalline anhydrous lenalidomide Form IV is conveniently prepared using any of the coformers selected from Resorcinol, Methyl Paraben & Saccharin.

Example 1a: [Using Crystalline Lenalidomide Saccharin Cocrystal]

Step-A:

To a suspension of Formula-II (50.0 g, 0.173 mol) in N,N-Dimethyl acetamide (250 mL, 5.0 vol.), 10% Pd/C (5.0 g, 0.1% w/w) was added into a hydrogenator. The mass was stirred at 25±5° C. under $H_2$ gas (90 psi) atmosphere. After completion of the reaction (Monitored through HPLC), the mass was filtered through celite, washed with N,N-Dimethyl acetamide (100 mL, 2.0 vol). The resulting filtrate subjected for Charcoal (5.0 g, 0.1% w/w) treatment, filtered through celite bed at 55±5° C., washed with N,N-Dimethyl acetamide (100 mL, 2.0 vol) to obtain Formula-I as a solution in DMAc (480 g).

Step-B:

To a solution of Formula-I in N,N-Dimethyl acetamide (480 g, 0.166 mol, Obtained from Step-A), Formula-IIIc (106.6 g, 0.582 mol) was added. The mass was concentrated under reduced pressure to a syrupy mass. It was contacted with MeOH (431 mL, 10.0 vol) at 25±5° C., filtered, and dried under reduced pressure at 55±5° C. to obtain a Formula-Vc as an off white solid (71.0 g).

Step-C:

A mixture of Formula-Vc (20.0 g, 0.032 mol) in N,N-Dimethyl acetamide (80.0 mL, 4.0 vol) was heated to 45-50° C., cooled to 25-30° C. Methanol (200 mL, 10.0 vol) was added. and the solid formed was filtered and dried at 80° C. under vacuum to obtain a Formula-I as an off-white solid.

Scheme-2: Preparation of crystalline anhydrous lenalidomide Form IV without insolation of Co-crystal

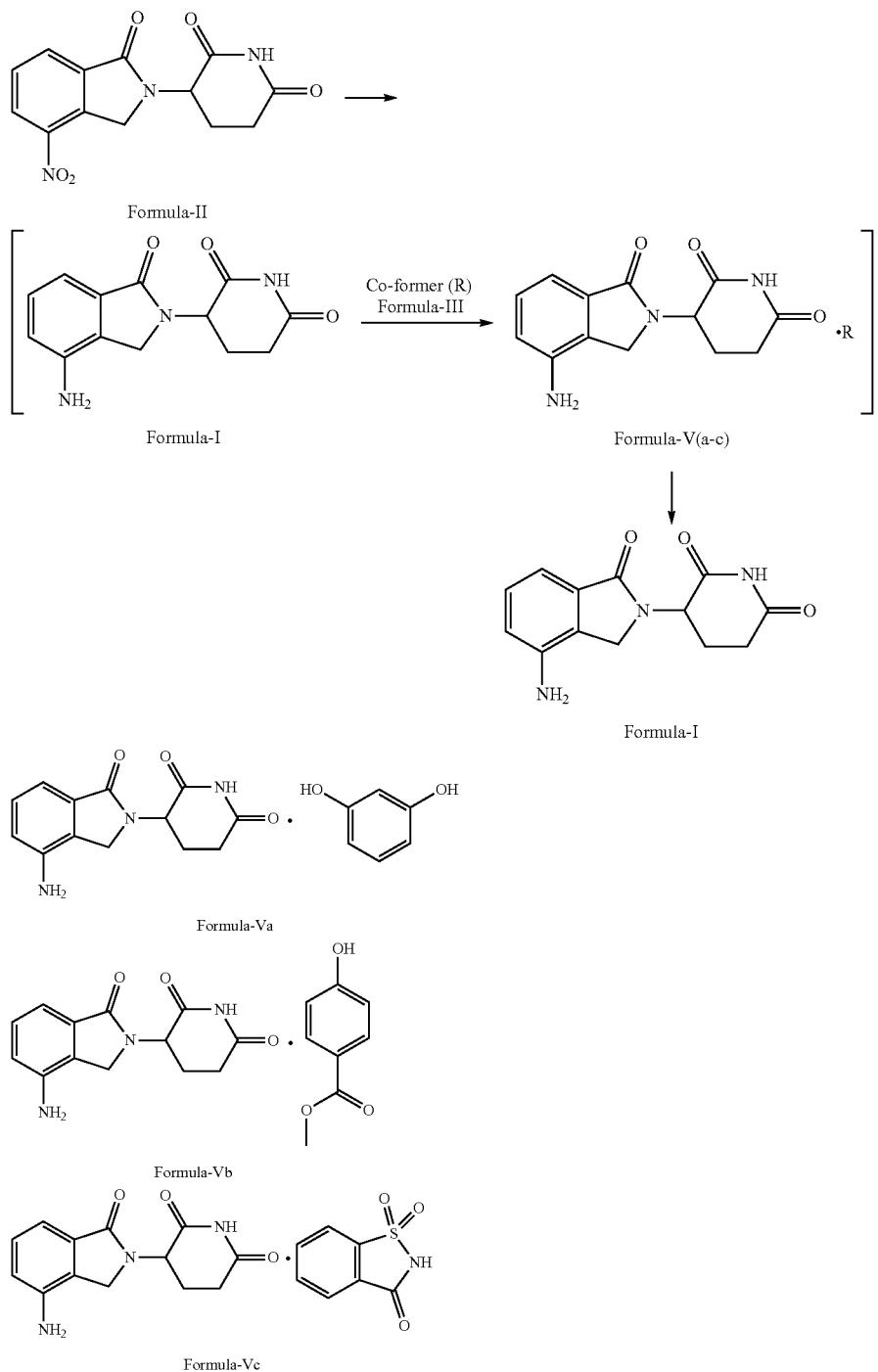

General Example-2

To a hydrogenator were added the Formula II, a suitable solvent and a hydrogenation catalyst. The reaction was stirred under H$_2$ atmosphere at a suitable temperature for a suitable amount of time. After completion of the reaction the reaction mass was cooled, filtered and the product as obtained in solution is subjected to charcoalisation. The charcoalised solution is treated with a suitable coformer R [wherein R is selected from Resorcinol, Methyl Paraben & Saccharin, stirred at a suitable temperature for a suitable amount of time and the lenalidomide cocrystal of Formula Vas obtained was taken to next step without isolation. The solution of lenalidomide cocrystal of Formula V is heated to a suitable temperature and cooled to room temperature followed by addition of a second solvent. The reaction mass was stirred for a suitable duration and isolated crystalline anhydrous lenalidomide Form IV.

As explained above the crystalline anhydrous lenalidomide Form IV is conveniently prepared using any of the coformers selected from Resorcinol, Methyl Paraben & Saccharin.

Example-2a

Step-a:

To a suspension of Formula-II (100 g, 0.345 mol.) in N,N-Dimethyl acetamide (500 mL, 5.0 vol.) was added 10% Pd/C (10.0 g, 0.1% w/w) into a hydrogenator. This reaction mass was stirred at 60±5° C. under H2 atmosphere for 3 h. After completion of the reaction indicated by the HPLC, mass was cooled to 25±5° C., filtered through Celite® bed, washed with N,N-Dimethyl acetamide (200 mL, 2.0 vol.). Filtrate was transferred into a reactor, charcoalised and the mass was filtered through Celite® bed at 45±5° C., washed with N,N-Dimethyl acetamide (200 mL, 2.0 vol.) to obtain Formula-I in DMAc as a yellow colour solution.

Step-b:

To a solution of Formula-I in N,N-Dimethyl acetamide (0.194 mol. obtained as in step-a) was contacted with saccharin as coformer of Formula-IIIc (125.67 g, 0.686 mol.). This mass was concentrated under reduced pressure to obtain a syrupy mass (Formula-Vc). This mass was treated with Methanol (1018 mL, 20.0 vol.), then stirred for 1 h at 25±5° C., filtered, washed with Methanol (101.74 mL, 2.0 vol.) and dried under reduced pressure at 60±5° C. for 16 h to obtain Formula-I as an off-white solid (36.5 g, 71.75%). The solid obtained was optionally treated with methanol (20.0 vol) at 25-30° C. and filtered. Compound was dried under reduced pressure at 60±5° C. for 16 h to obtain crystalline anhydrous lenalidomide Form IV of Formula-I as an off white solid.

Example-2b

Step-a:

To a suspension of Formula-II (100 g, 0.345 mol.) in N,N-Dimethyl acetamide (500 mL, 5.0 vol.) was added 10% Pd/C (10.0 g, 0.1% w/w) into a hydrogenator. This reaction mass was stirred at 60±5° C. under $H_2$ atmosphere for 3 h. After completion of the reaction indicated by the HPLC, mass was cooled to 25±5° C., filtered through Celite® bed, washed with N,N-Dimethyl acetamide (200 mL, 2.0 vol.). Filtrate was transferred into a reactor, charcoalised and the mass was filtered through Celite® bed at 45±5° C., washed with N,N-Dimethyl acetamide (200 mL, 2.0 vol.) to obtain Formula-I in Dimethyl acetamide as a yellow colour solution.

Step-b:

Compound of Formula-I in N,N-Dimethyl acetamide (0.0194 mol, obtained as in step-a) was concentrated under reduced pressure to a transparent syrupy mass. Formula IIIc (0.039 mol, 2.0 equiv) was added to the mass and charged N,N-Dimethyl acetamide (5.0 mL, 1.0 vol). This mass was stirred for 6-12 h at 25-30° C., methanol (10 vol) was added, stirred for 1 h at 25-30° C., filtered and dried at 45-50° C. under vacuum to obtain Formula-I as an off-white solid.

Example-2c

Step-a:

Performed as per step-a of Example-2b.

Step-b:

A solution of Formula-I in N,N-Dimethyl acetamide (0.388 mol) was added with Saccharin of Formula IIIc (1.356 mol). This solution was concentrated under reduced pressure to a transparent syrupy mass. This mass was added to Methanol (10.0 vol) at 25±5° C., then stirred for 1 h at 25±5° C. and filtered. It was dried under reduced pressure at 60±5° C. for 16 h to obtain Formula-I as an off-white solid.

Example-2d

Step-a:

Performed as per step-A&B of Example-1a.

Step-b:

A slurry of Formula-Vc (150 g, 0.239 mol.) in N,N-Dimethyl acetamide (2.5 vol.) was heated to 55±5° C. under stirring to obtain a clear solution. This solution was cooled to 25±5° C. It was added to Methanol (10.0 vol.), stirred for 1.5 h at 25±5° C., filtered and washed with Methanol (2.0 vol.). Compound was dried under reduced pressure at 60±5° C. for 16 h to obtain Formula-I as an off-white solid (38.50 g).

Scheme-3: Preparation of crystalline Resorcinol Co-crystal

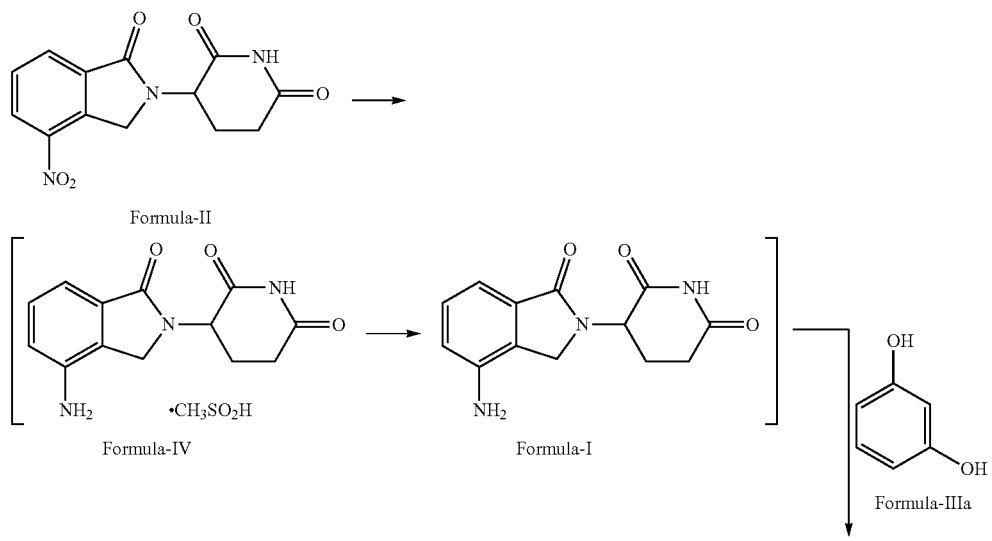

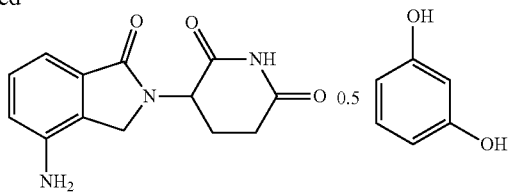

Formula-Va

Example 3a

To a suspension of compound of Formula II (7.00 g), Water (105 mL, 15 vol), Methane sulfonic acid (3.92 mL) and Pd/C (10% loading, 50% wet, 0.70 g), hydrogen gas (90 psi) was purged at 25-30° C. The progress of the reaction was monitored by HPLC. After the completion of the reaction, the mass was filtered, washed with water (20 mL). pH of the filtrate was adjusted to by adding triethylamine (9.0 mL). The slurry obtained was washed with water (2×35 mL) followed by the addition of compound of Formula IIIa (4.58 g). The mass was heated between 65 and 70° C. for 5-6 h. It was cooled between 60 and 70° C., filtered and dried at 45-50° C. under reduced pressure to obtain Lenalidomide-Resorcinol co-crystal of Formula Va as a crystalline solid. It was characterized by $^1$H NMR, DSC, FT-IR, PXRD and TGA.

Example 3b

To a suspension of compound of Formula I (10.0 g) in water (100 mL, 10 vol) was added compound of Formula IIIa (6.37 g, 1.50 equiv). The reaction mixture was heated between 65 and 70° C. for 5 to 6 h. It was then filtered under hot condition and dried under vacuum at 45-50° C. to obtain Lenalidomide-Resorcinol co-crystal of Formula Va as a crystalline solid.

Example 3c

To a suspension of compound of Formula I (1.0 g) in Ethyl acetate (10 mL, 10 vol) was added compound of Formula IIIa (1.70 g, 4.0 equiv). The reaction mixture was stirred between 25 and 30° C. for 5 to 6 h. It was then filtered and dried under vacuum at 45-50° C. to obtain Lenalidomide-Resorcinol co-crystal of Formula Va as a crystalline solid.

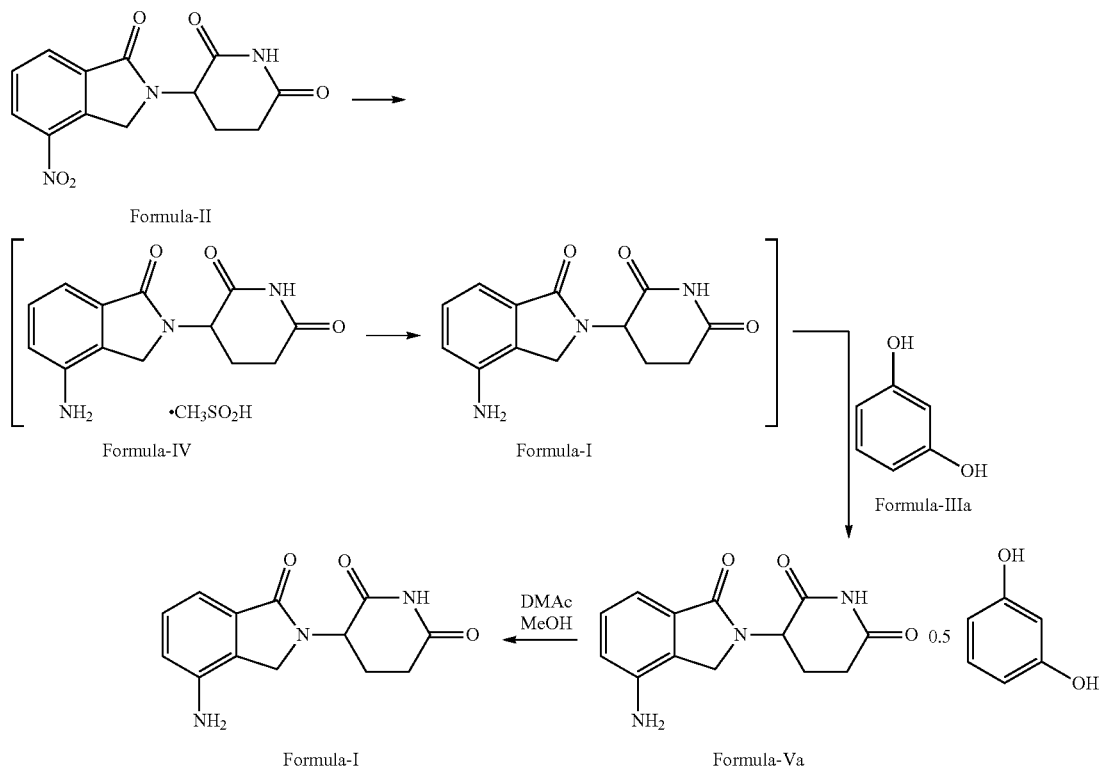

Scheme-4: Process for the preparation of crystalline anhydrous lenalidomide Form IV from Resorcinol co-crystal

Example-4

A slurry of Formula-Va (5.0 g, 0.0192 mol obtained as per the procedure mentioned in Example-3a) in N,N-Dimethyl acetamide (20.0 mL, 4.0 vol.) was heated to 65±5° C. under stirring to obtain a clear solution. Solution was cooled to 25±5° C., this mass was contacted with Methanol (50.0 mL, 10.0 vol.) at 25±5° C. and filtered. Compound was dried under vacuum at 60±5° C. for 16 h to obtain Formula-I as crystalline anhydrous lenalidomide Form IV an off white solid (3.50 g, 70%).

The invention claimed is:

1. A lenalidomide Saccharin co-crystal of Formula Vc,

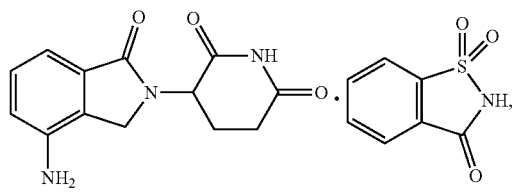

Formula Vc characterised by an XPRD pattern comprising major peaks at approximately 14.99±0.2, 16.05±0.2, 19.14±0.2, 20.14±0.2, 22.53±0.2, 25.17±0.2 and 25.78±0.2, degrees 2θ.

Figure 8:
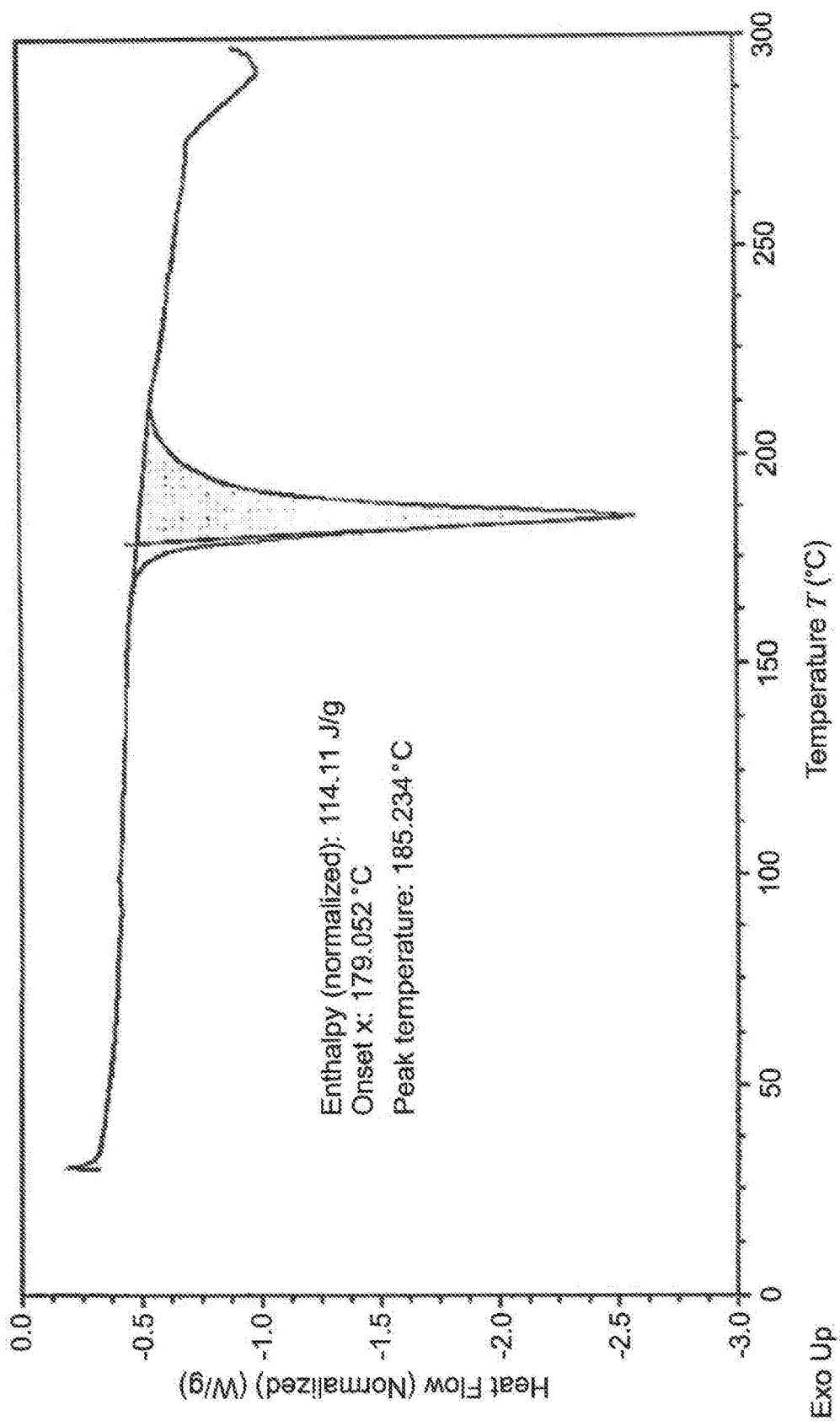
FIG. 8: Illustrates the DSC thermogram of the crystalline Lenalidomide-Saccharin co-crystal of Formula Vc.
Figure 9:
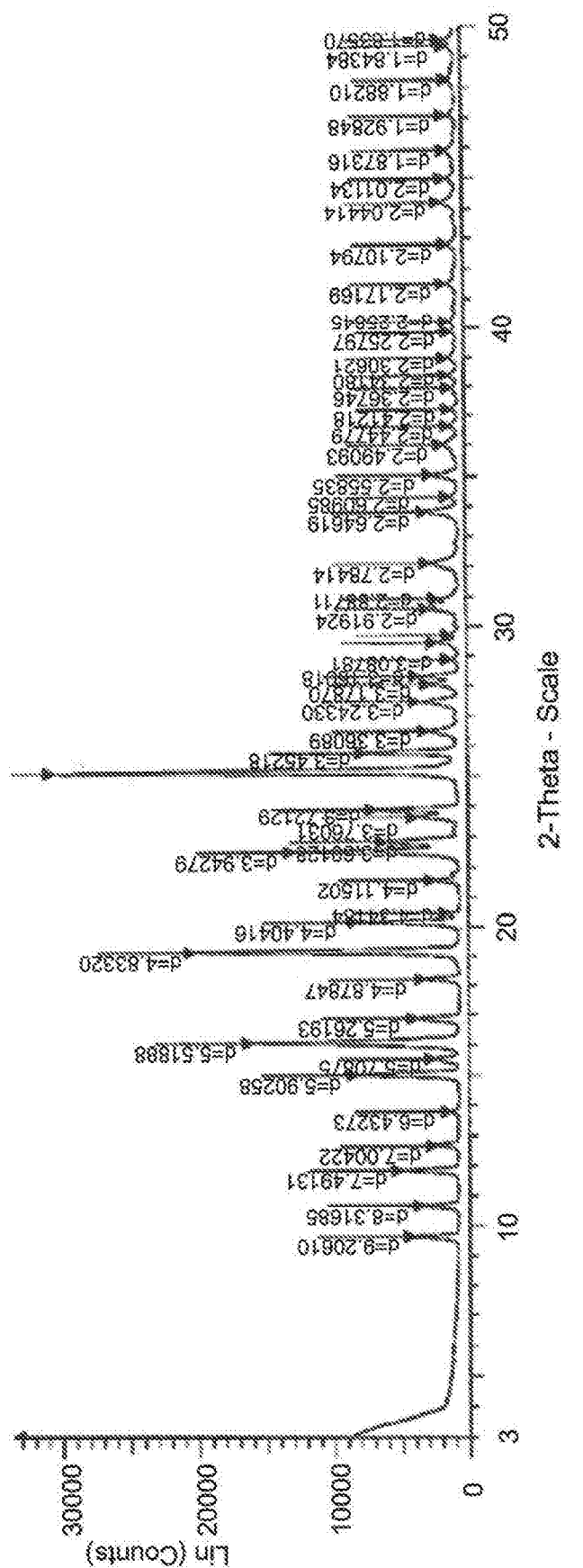
FIG. 9: Illustrates the PXRD of the crystalline Lenalidomide-Saccharin co-crystal of Formula Vc.
Figure 10:
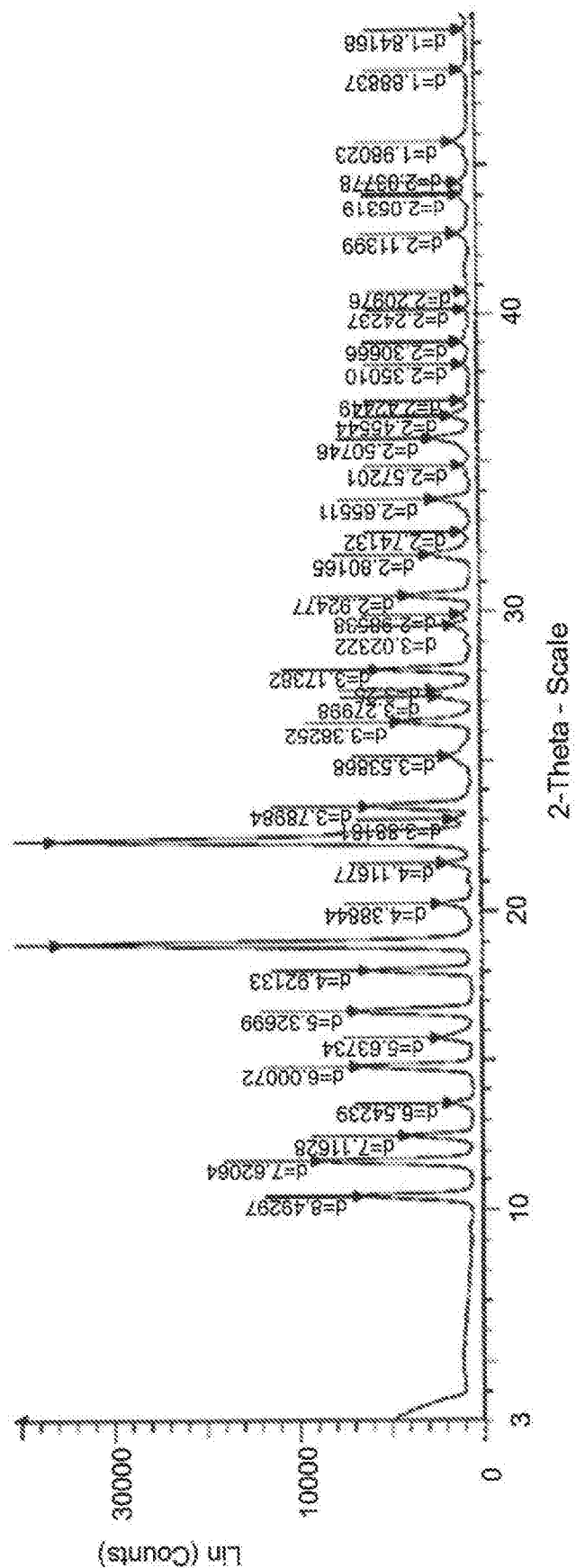
FIG. 10: Illustrates the PXRD of the crystalline anhydrous lenalidomide Form IV.

2. The lenalidomide Saccharin co-crystal of claim 1, characterised by a DSC having an endotherm at around 185° C. and the DSC pattern in accordance with FIG. 8.

3. A process for the preparation of a lenalidomide Saccharin co-crystal of Formula Vc of claim 1, the process comprising the following steps, reducing a Nitro intermediate of Formula II

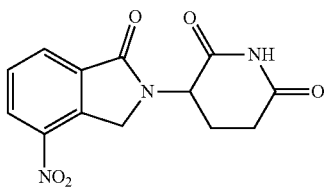

Formula-II using a hydrogenation catalyst in a solvent selected from an organic solvent, an aqueous solvent, and a combination thereof at a temperature ranging between 25 and 70° C. to obtain a reaction mixture containing lenalidomide of Formula I

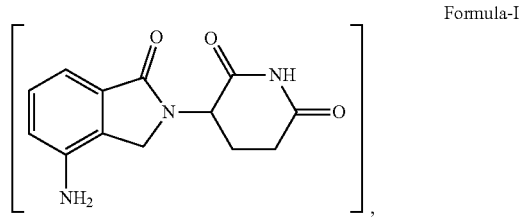

Formula-I in situ treating of lenalidomide of Formula I with conformer Saccharin in an amount ranging between 0.5 and 10 equivalents

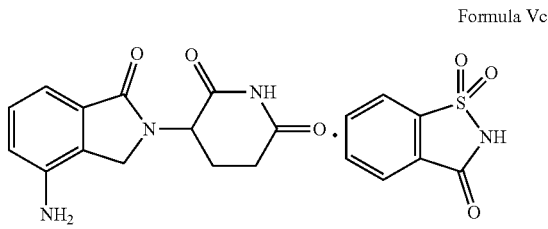

Formula Vc obtaining crystalline lenalidomide Saccharin co-crystal of Formula Vc.

4. The process for preparation of crystalline lenalidomide Saccharin co-crystal of claim 3 of Formula Vc, wherein the organic solvent is selected from N,N,Dimethyl acetamide a $C_1$-$C_3$ alcohol, and a combination thereof.

5. The process for preparation of crystalline lenalidomide Saccharin co-crystal of claim 4 of Formula Vc, wherein the $C_1$-$C_3$ alcohol is methanol.

* * * * *